(12) United States Patent
Endo et al.

(10) Patent No.: US 8,900,410 B2
(45) Date of Patent: Dec. 2, 2014

(54) FINE FIBROUS CELLULOSIC MATERIAL AND PROCESS FOR PRODUCING THE SAME

(75) Inventors: Takashi Endo, Kure (JP); Seung-Hwan Lee, Kure (JP); Yoshikuni Teramoto, Kure (JP); Noriko Tanaka, Kure (JP); Manami Sakai, Kure (JP); Naomi Kadotani, Kure (JP)

(73) Assignee: National Institute of Advanced Industrial Science and Technology, Kure-shi, Hiroshima (JP)

( * ) Notice: Subject to any disclaimer, the term of this patent is extended or adjusted under 35 U.S.C. 154(b) by 0 days.

(21) Appl. No.: 13/608,452

(22) Filed: Sep. 10, 2012

(65) Prior Publication Data

US 2013/0052695 A1 Feb. 28, 2013

Related U.S. Application Data

(62) Division of application No. 12/450,570, filed as application No. PCT/JP2008/056103 on Mar. 28, 2008, now abandoned.

(30) Foreign Application Priority Data

Mar. 30, 2007 (JP) ................................ 2007-094085

(51) Int. Cl.
*D21F 11/00* (2006.01)
(52) U.S. Cl.
USPC ................. 162/115; 162/27; 162/28; 162/158
(58) Field of Classification Search
USPC ............................ 162/27, 28, 158, 179, 115
See application file for complete search history.

(56) References Cited

U.S. PATENT DOCUMENTS 5,964,983 A 10/1999 Dinand et al.

FOREIGN PATENT DOCUMENTS

| GB | 2066145 A | 7/1981 |
|----|-----------|--------|
| JP | 55-9758 | 1/1980 |
| JP | 59-146594 | 8/1984 |
| JP | 61-242591 | 10/1986 |
| JP | 63-137690 | 6/1988 |
| JP | 4-81813 | 3/1992 |
| JP | 11-501684 | 2/1999 |
| JP | 2006-136263 | 6/2006 |

OTHER PUBLICATIONS

Takashi Endo et al., Bisai Sen ika shita Mokushitsu Biomass no Ekitai Nenryo Oyobi Keisei Zairyo Tenkan, pp. 002, Jul. 20, 2007 (3 pages).
Takashi Endo et al., Conversion of Woody Biomass into Liquid Fuel and Molding Material by Milling Technology, pp. 33-39, vol. 38, No. 12 (2006) (8 pages).
Herrick et al "Microfibrillated cellulose: morphology and accessibility," Journal of Applied Polymer Science: Applied Polymer Symposium, vol. 37 Conference 9, Cellulose Conference, Syracuse NY May 1982, published Jan. 1983, 797-813.
Paakko et al, "Enzymatic Hydrolysis Combined with Mechanical Shearing and High-Pressure Homogenization for Nanoscale Cellulose Fibrils and Strong Gels" Biomacromolecules, 2007, vol. 8(6) 1934-1941.
Turbak et al "Microfibrillated cellulose, A new Cellulose Product: Properties, Uses, and commercial potential", Journal of Applied Polymer Science: Applied Polymer Symposium, vol. 37 Conference 9, Cellulose Conference, Syracuse NY May 1982, published Jan 1983, 815-827.
Zou, H et al. "Effect of Hemicellulose Content in Kraft Brownstock on Oxygen Delignification", Proceedings of the 2002 TAPPI Pulping & Engineering Conference, San Diego, CA, Sep. 7 thru 11, 2002.

*Primary Examiner* — Mark Halpern
(74) *Attorney, Agent, or Firm* — Flynn, Thiel, Boutell & Tanis, P.C.

(57) ABSTRACT

A fine fibrous cellulosic material containing cellulose, hemicellulose and lignin, in which the fine fibrous cellulosic material has a width of 1 μm or less and a length of 5,000 μm or less and is used for glycation reaction by hydrolysis.

5 Claims, 4 Drawing Sheets

FIG.7(a)
FIG.7(b)
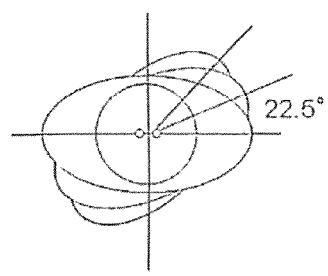
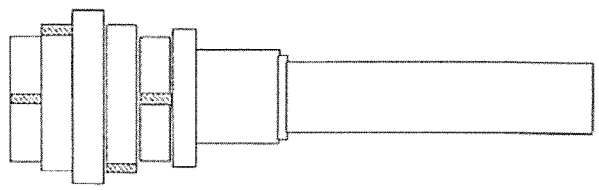
FIG.8
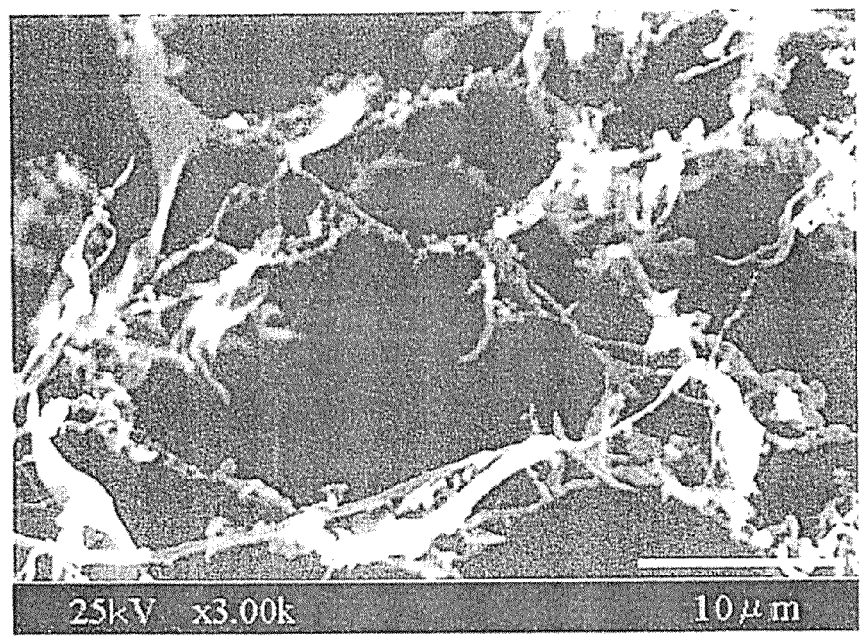

FINE FIBROUS CELLULOSIC MATERIAL AND PROCESS FOR PRODUCING THE SAME

This is a divisional of prior U.S. application Ser. No. 12/450,570 filed Feb. 12, 2010, which was the National Stage of International Application No. PCT/JP2008/056103, filed Mar. 28, 2008.

TECHNICAL FIELD

The present invention relates to: fine fibrous cellulosic materials; processes for producing fine fibrous cellulosic materials; and processes for producing saccharides.

BACKGROUND ART

The principal chemical constituents of plant bodies such as wood and vegetation are cellulosic materials such as cellulose, hemicellulose and lignin. Of the cellulosic materials, cellulose and hemicellulose are high-molecular weight materials in which saccharides are bound in a straight- or branched-chain shape.

Such cellulosic materials are known to be converted into saccharides by hydrolysis. Such hydrolysis methods include an acid hydrolysis method and an enzymatic hydrolysis method.

However, the efficient hydrolysis of a cellulosic material is not easy.

For example, in hydrolysis using an acid, although a reaction proceeds in an extremely short time on the minute time scale, reaction control is difficult due to the occurrence of heat generation. Even if the reaction control is enabled, constituents in a cellulosic material are prone to be excessively decomposed and carbonized, and therefore a saccharide cannot be obtained in a sufficient yield.

In hydrolysis using an enzyme, although constituents in a cellulosic material are not excessively decomposed, the proceeding of a hydrolysis reaction is slow, sometimes requires 48 hours or longer. There may be also a method using a large amount of an enzyme for increasing the yield of an obtained saccharide and a hydrolysis rate, which method has the disadvantage of increasing the cost.

In contrast, research has been conducted on methods of undoing the entanglement of lignin with cellulose and hemicellulose by carrying out some sort of treatment prior to the enzymatic hydrolysis of cellulosic materials.

For example, a method in which wood is finely pulverized and then the enzymatic hydrolysis of the pulverized wood is performed (for example, see Patent Document 1 or 2); a method in which acid is added to a plant body containing lignocellulose and the mixture is heated by microwaves and subjected to acid hydrolysis (for example, see Patent Document 3); a method in which a cellulose-containing material is treated with a dimethylformamide solution containing nitrogen oxides and thereafter subjected to enzymatic hydrolysis (for example, see Patent Document 4); a method in which a lignocellulose-based biomass is treated with pressurized hot water and subjected to mechanical pulverization and then to enzymatic hydrolysis (for example, see Patent Document 5); and the like are disclosed.

Patent Document 1 Japanese Patent Application Laid-Open Publication No. 55-9758
Patent Document 2 Japanese Patent Application Laid-Open Publication No. 63-137690
Patent Document 3 Japanese Patent Application Laid-Open Publication No. 59-146594
Patent Document 4 Japanese Patent Application Laid-Open Publication No. 61-242591
Patent Document 5 Japanese Unexamined Patent Application Publication No. 2006-136263

DISCLOSURE OF THE INVENTION

Problem to be Solved by the Invention

However, in the above-mentioned methods described in Patent Documents 1-5, although cellulosic materials can be pulverized, the entanglement of lignin with cellulose and hemicellulose cannot be sufficiently undone.

Accordingly, even if the hydrolysis of cellulosic materials is performed, saccharides cannot be obtained in a sufficient yield by the above-mentioned methods described in Patent Documents 1-5.

The present invention is desired with respect to the above-mentioned circumstances and is directed at providing: a fine fibrous cellulosic material capable of producing a saccharide in a high yield by hydrolysis; a process for producing the fine fibrous cellulosic material from a cellulosic material; and a process for producing the saccharide using the fine fibrous cellulosic material.

Means for Solving the Problem

The present inventors undertook thorough research in order to solve the above-mentioned problem and thus found that the respective aggregation units of cellulose, hemicellulose and lignin form blocks, which are mixed to form a rigid network structure, in a cellulosic material. Specifically, the molecular chains of cellulose regularly self-assemble just after in vivo biosynthesis to form crystalline microfibrils having a width of several nanometers and assemble, together with amorphous hemicellulose and lignin, to be fibrous.

The microfibrils of cellulose regularly align in a specific direction to form a cell wall; and hemicellulose and lignin cover the periphery of the microfibrils of the cellulose or fill between the microfibrils of the cellulose and function as an adhesive.

As a result of further extensive research on the basis of these findings, the present inventors found that the above-mentioned problem can be solved by making cellulosic materials fine fibrous have a width of 1 μm or less and a length of 5,000 μm or less, and the invention was thus accomplished.

Specifically, the present invention is (1) a fine fibrous cellulosic material containing cellulose, hemicellulose and lignin, wherein the fine fibrous cellulosic material has a width of 1 μm or less and a length of 5,000 μm or less and is used for glycation reaction by hydrolysis.

The present invention is (2) the fine fibrous cellulosic material according to the above-mentioned (1), wherein the hydrolysis is enzymatic hydrolysis.

The present invention is (3) a process for producing a fine fibrous cellulosic material used for glycation reaction by hydrolysis, including: carrying out mechanical pulverization of a mixture prepared by mixing a cellulosic material containing cellulose, hemicellulose and lignin with a fibrillation material for fibrillating the cellulosic material; and making a fine fibrous cellulosic material having a width of 1 μm or less and a length of 5,000 μm or less from the cellulosic material.

The present invention is (4) the process for producing a fine fibrous cellulosic material according to the above-mentioned (3), wherein the mechanical pulverization is performed by a ball mill, a rod mill, a bead mill, a disk mill or a mixer.

The present invention is (5) the process for producing a fine fibrous cellulosic material according to the above-mentioned (3), wherein the mechanical pulverization is performed by a batch-type or continuous-type extruder.

The present invention is (6) the process for producing a fine fibrous cellulosic material according to the above-mentioned (3), wherein the mechanical pulverization is performed under a temperature condition of 20-350° C. and/or a pressure condition of 0.1-20 MPa.

The present invention is (7) the process for producing a fine fibrous cellulosic material according to the above-mentioned (3), comprising: preliminarily pulverizing the cellulosic material to make a chip-like, fibrous or powdered fine cellulosic material; thereafter mixing the fine cellulosic material with the fibrillation material; and performing the mechanical pulverization.

The present invention is (8) the process for producing a fine fibrous cellulosic material according to the above-mentioned (3), wherein a mixing rate of the fibrillation material is 0.01-200 parts by mass with respect to 1 part by mass of cellulosic material.

The present invention is (9) the process for producing a fine fibrous cellulosic material according to the above-mentioned (3), wherein the fibrillation material is water.

The present invention is (10) the process for producing a fine fibrous cellulosic material according to the above-mentioned (3), wherein the fibrillation material is a low-molecular weight compound.

The present invention is (11) the process for producing a fine fibrous cellulosic material according to the above-mentioned (3), wherein the fibrillation material is a high-molecular weight compound.

The present invention is (12) the process for producing a fine fibrous cellulosic material according to the above-mentioned (3), wherein the fibrillation material is a fatty acid.

The present invention is (13) the process for producing a fine fibrous cellulosic material according to the above-mentioned (3), wherein the fibrillation material is constituted of water and a low-molecular weight compound; and a mixing rate of the low-molecular weight compound is 0.1-99.9 mass % with respect to a total weight of the fibrillation material.

The present invention is (14) the process for producing a fine fibrous cellulosic material according to the above-mentioned (3), wherein the fibrillation material is constituted of water and a high-molecular weight compound; and a mixing rate of the high-molecular weight compound is 0.1-99.9 mass % with respect to a total weight of the fibrillation material.

The present invention is (15) the process for producing a fine fibrous cellulosic material according to the above-mentioned (3), wherein the fibrillation material is constituted of water and a fatty acid; and a mixing rate of the fatty acid is 0.1-99.9 mass % with respect to a total weight of the fibrillation material.

The present invention is (16) the process for producing a fine fibrous cellulosic material according to the above-mentioned (3), wherein the fibrillation material is constituted of water and an inorganic alkali; and a mixing rate of the inorganic alkali is 0.1-99.9 mass % with respect to a total weight of the fibrillation material.

The present invention is (17) a process for producing a saccharide, including: carrying out mechanical pulverization of a mixed liquid prepared by mixing a cellulosic material containing cellulose, hemicellulose and lignin as well as a fibrillation material for fibrillating the cellulosic material with an enzyme; and, concurrently with making a fine fibrous cellulosic material from the cellulosic material, carrying out enzymatic hydrolysis of the fine fibrous cellulosic material with the enzyme to make a saccharide.

The present invention is (18) a process for producing a saccharide, including: providing a saccharide by performing acid hydrolysis or enzymatic hydrolysis of a fine fibrous cellulosic material provided by the process for producing a fine fibrous cellulosic material according to any one of the above-mentioned (3) to (16).

A structure in which the above-mentioned (1) to (18) are appropriately combined can be adopted if meeting the object of the invention.

Effect of the Invention

In the fine fibrous cellulosic material of the present invention, a cellulosic material made to have a width of 1 μm or less and a length of 5,000 μm or less results in an improvement in hydrolysis (glycation reaction) rate and yield of a saccharide to be obtained.

The reason why the yield of a saccharide is improved as described above is unclear but is likely to be that the fine fibrous cellulosic material made to have a predetermined width, length or aspect ratio (hereinafter generally referred to as "size") results in the increase in surface area and the facilitation of the adhesion of an acid or an enzyme to the fine fibrous cellulosic material as well as in the increase in the number of reaction points of an enzyme or an acid which can be hydrolyzed. However, its causes are not limited thereto.

An aspect ratio as described herein refers to a ratio between a long side (length) and a short side (width).

The fine fibrous cellulosic material having the aforementioned size allows the sufficient undoing of the entanglement of lignin with cellulose and hemicellulose.

Accordingly, the hydrolysis of such a fine fibrous cellulosic material promotes the hydrolysis to obtain a saccharide in a high yield.

Here, the above-mentioned hydrolysis is preferably enzymatic hydrolysis.

In this case, a saccharide can be inexpensively obtained since a cellulosic material can be sufficiently hydrolyzed even with a comparatively small amount of enzyme.

In case of enzymatic hydrolysis, an excessively decomposed product is not generated and a side reaction is inhibited since the hydrolyze can be carried out at low temperature.

In a process for producing a fine fibrous cellulosic material according to the present invention, the mechanical pulverization of a mixture prepared by mixing a cellulosic material with a fibrillation material is carried out to obtain a fine fibrous cellulosic material having a width of 1 μm or less and a length of 5,000 μm or less as described above.

In this case, in the process for producing a fine fibrous cellulosic material, the mechanical pulverization of the mixture prepared by mixing the cellulosic material with the fibrillation material is carried out, whereby the fibrillation material enters between cellulose microfibrils to widen these gaps and concurrently damage the texture, and the hemicellulose and the lignin which are adhered to the cellulose microfibrils are removed.

As a result, the cellulosic material will be undone to a microfibril which is a minimum aggregation unit of a cellulose molecular chain.

Accordingly, the process for producing a fine fibrous cellulosic material provides a fine fibrous cellulosic material which is fibrillated into a cellulose microfibril in the pure form that is most efficient for a hydrolysis reaction while a cellulosic material is in a solid state without inhibiting the hydrolysis reaction.

Furthermore, in the process for producing a fine fibrous cellulosic material, the unique crystallinity of a cellulosic material is maintained in the obtained fine fibrous cellulosic material since the bundle of the cellulosic material formed by assembling cellulose microfibrils is undone to form the individual cellulose microfibrils. In other words, surface or internal cellulose molecules provide cellulose microfibrils having a crystallinity which are scarcely subjected to the disorder of the sequence and orientation of molecular chains or chemical modification.

Accordingly, the process for producing a fine fibrous cellulosic material provides a fine fibrous cellulosic material, of which the hydrolysis reaction easily proceeds, even in the case of a cellulose having a high crystallinity. Particularly, when the hydrolysis is enzymatic hydrolysis, the surface of cellulose microfibrils is not subjected to strong modification, and therefore the hydrolysis easily proceeds without inhibiting the substrate specificity of an enzyme.

Furthermore, in the process for producing a fine fibrous cellulosic material, an obtained fine fibrous cellulosic material need not be hydrolyzed under severe conditions such as strong chemical agents such as sulfuric acid and high-pressure and high-temperature water since the cellulosic material is a fibrillated cellulose microfibril.

Therefore, the reaction control is easy, and a saccharide can be efficiently produced from the fine fibrous cellulosic material without generating an excessively decomposed product and without applying great pulverization energy.

In the production process of a fine fibrous cellulosic material, when a cellulosic material is derived from a plant (including algae) and has a chip-like, fibrous or powdered shape, a plant tissue is partially damaged prior to mechanical pulverization, and therefore a fine fibrous cellulosic material can be efficiently produced in a comparatively short time.

In the production process of a fine fibrous cellulosic material, a fine fibrous cellulosic material can be comparatively easily produced by performing the mechanical pulverization by a ball mill, a rod mill, a bead mill, a disk mill or a mixer.

In addition, variations in size of an obtained fine fibrous cellulosic material are reduced. Then, a hydrolysis reaction easily proceeds.

In the production process of a fine fibrous cellulosic material, a fine fibrous cellulosic material can be efficiently produced in a shorter time by performing the mechanical pulverization by a batch-type or continuous-type extruder.

In the production process of a fine fibrous cellulosic material, a fine fibrous cellulosic material can be efficiently produced in a shorter time by the mechanical pulverization under a temperature condition of 20-350° C. and/or a pressure condition of 0.1-20 MPa.

In the production process of a fine fibrous cellulosic material, a cellulosic material is preliminarily pulverized to make a fine cellulosic material, followed by mixing the fine cellulosic material with a fibrillation material and performing mechanical pulverization, and a slurry fine fibrous cellulosic material having a low aspect ratio is thus obtained.

Such a fine fibrous cellulosic material has a high flowability, is easy to, e.g., transport with a pump, and is thus excellent in handleability.

In addition, high flowability facilitates the proceeding of hydrolysis. In a conventional cellulosic material, the viscosity of a slurry tends to becomes high to deteriorate the flowability.

In the production process of a fine fibrous cellulosic material, when a mixing rate of a fibrillation material is 0.01-200 parts by mass with respect to 1 part by mass of cellulosic material, the cellulosic material is surely mechanically pulverized, and a fine fibrous cellulosic material having a predetermined shape can be produced.

In a process for producing a saccharide of the present invention, an enzyme is mixed with a cellulosic material containing cellulose, hemicellulose and lignin and a fibrillation material for fibrillating the cellulosic material, and a saccharide can be obtained from a cellulosic material in a high yield at a time by mechanical pulverization.

In the production process of a saccharide, hemicellulose and lignin are removed by the fine fiberization of the cellulosic material, cellulose microfibrils appear on a surface, and the enzyme approaches and is adsorbed to the cellulose microfibrils to hydrolyze the fine fibrous cellulosic material.

In addition, new gaps are formed in the cellulose microfibrils by the hydrolysis, a fibrillation material enters thereinto, and fibrillation further proceeds.

As described above, in accordance with the production process of a saccharide, fibrillation and enzymatic hydrolysis are simultaneously carried out to produce a mutual synergistic effect.

In the process for producing the saccharide of the present invention, acid hydrolysis or enzymatic hydrolysis is performed using the above-mentioned fine fibrous cellulosic material, and therefore the saccharide can be produced in a high yield.

BRIEF DESCRIPTION OF THE DRAWINGS

FIG. 7 (*a*) is a front view illustrating the segment-type screw used in Example 48; and FIG. 7 (*b*) is a side view of the segment-type screw.

FIG. 8 is a scanning electron micrograph of the sample 48 obtained in Example 48.

DESCRIPTION OF THE REFERENCE NUMERALS

Figure 1:
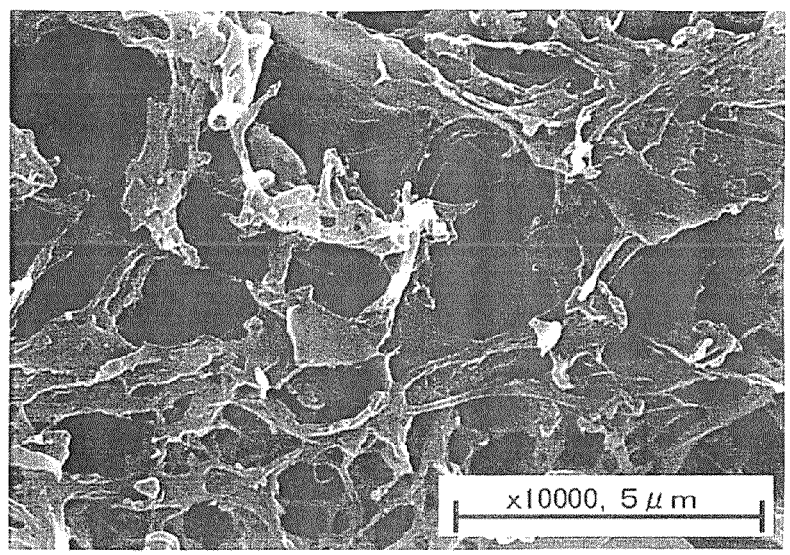
FIG. 1 is a scanning electron micrograph of a sample 2 obtained in Example 2.

1 Kneading portion
2 Segment-type screw
10 Small segment mixer

BEST MODE FOR CARRYING OUT THE INVENTION

A preferred embodiment of the present invention is described in detail below.

A fine fibrous cellulosic material according to the present embodiment is constituted of cellulose materials including cellulose, hemicellulose and lignin and has fine fibrous form.

As used herein, a cellulosic material in accordance with the present embodiment refers to a mixture including cellulose, hemicellulose and lignin.

Such cellulosic materials are obtained from, e.g., plants such as wood, vegetation, agricultural products and raw cotton.

A fine fibrous cellulosic material has a width of 1 μm or less, preferably 0.1 μm or less, further preferably 3-5 nm, and a length of 5,000 μm or less, preferably 50 μm or less.

The fine fibrous cellulosic material made to have the sizes in the above-mentioned ranges allows sufficient undoing of entanglement of lignin with cellulose and hemicellulose.

As a result, a hydrolysis (glycation reaction) rate is improved, and the yield of a saccharide to be obtained is improved.

When the fine fibrous cellulosic material is used in glycation reaction by hydrolysis, it is preferable that the hydrolysis be enzymatic hydrolysis.

The fine fibrous cellulosic material has many exposed surfaces, which is approached by an enzyme and to which the enzyme is adsorbed, to facilitate hydrolysis, and a space, into which the enzyme easily moves, is formed around the fine fibrous cellulosic material.

Therefore, the hydrolysis of the cellulosic material is sufficiently performed with a comparatively small amount of enzyme, and a saccharide can be inexpensively provided. Details of hydrolysis will be described below.

A process for producing a fine fibrous cellulosic material will be described below.

The fine fibrous cellulosic material is produced by mixing cellulosic materials with fibrillation materials for fibrillating the cellulosic materials and performing mechanical pulverization. Specifically, the cellulosic materials are mixed with the fibrillation materials and the mixture is mechanically pulverized; therefore the cellulosic materials enter between the microfibrils of cellulose to widen these gaps and concurrently damage the texture; and the fine fibrous cellulosic material having the above-mentioned predetermined sizes is provided.

The cellulosic material is preferably derived from a plant.

Cellulosic materials derived from plants self-assemble just after biosynthesis to form microfibrils of cellulose and therefore have an extremely large surface area without a change in the orientation of cellulose molecular chains by being fibrillated into microfibrils.

The fibrillation material functions as a medium for fibrillating a cellulosic material.

As such fibrillation material, which is not limited in particular, water, a low-molecular weight compound, a high-molecular weight compound, a fatty acid or inorganic alkali is preferably used. One of these may be singly used or two or more of these may be mixedly used. As described below, the inorganic alkali is used together with water.

When the fibrillation material is water, water molecules are small, therefore the water easily enters into the fine pores and gaps of a tissue and further easily enters between cell walls containing a large amount of ingredients having a high affinity for water, such as cellulose or hemicellulose, and therefore the tissue can be swollen.

In addition, there is such an advantage that the water further enters between cellulose microfibrils by pulverization energy due to mechanical pulverization to facilitate the proceeding of fibrillation.

When the fibrillation material is a low-molecular weight compound, there is such an advantage that the low-molecular weight compound enters between tissues or cell walls and acts like a wedge to facilitate the proceeding of fibrillation.

When the fibrillation material is a high-molecular weight compound, a tissue is partially melted and flowability is enhanced by pressure, shearing force or heat during mechanical pulverization.

Then, there is such an advantage that the action to adhere to and remove a tissue or a cell wall surface is further effected and the high-molecular weight compound enters into a formed gap to facilitate the proceeding of fibrillation.

When the fibrillation material is a fatty acid, the fatty acid exhibits an affinity for hemicellulose, in which the side chain of a constituent saccharide has an acetyl group, and easily enters between tissues or cell walls.

In addition, there is such an advantage that a hydroxyl group of cellulose, hemicellulose or lignin is partially esterified by pressure, shearing force or heat during mechanical pulverization, thereby easily widening between tissues to facilitate the proceeding of fibrillation.

Of these, as fibrillation materials, water is preferably mixedly used with a low-molecular weight compound, a high-molecular weight compound, a fatty acid or inorganic alkali. In this case, the low-molecular weight compound, the high-molecular weight compound and the fatty acid are preferably water-soluble.

The low-molecular weight compound is preferably at least one selected from the group consisting of alcohols, ethers, ketones, sulfoxides, amides, amines, aromatics and morpholines.

The alcohols include methanol, ethanol, 1-propanolol, 2-propanolol, 1-butanol, t-butanol, alkylene glycols such as ethylene glycol, trimethylene propanolol, butanediol, glycerin, etc. One of these may be singly used or two or more of these may be mixedly used.

The ethers include 1,4-dioxane, etc. One of these may be singly used or two or more of these may be mixedly used.

The ketones include acetone, methyl ethyl ketone, diethyl ketone, methyl propyl ketone, stearyl ketene dimers, etc. One of these may be singly used or two or more of these may be mixedly used.

The sulfoxides include dimethylsulfoxide, bisphenyl sulfoxides, bishydroxyphenyl sulfoxides such as bis(4-hydroxyphenyl)sulfoxide, bis(3,5-dimethyl-4-hydroxyphenyl)sulfoxide, bis(2,3-dihydroxyphenyl)sulfoxide, bis(5-chloro-2,3-dihydroxyphenyl)sulfoxide, bis(2,4-dihydroxyphenyl)sulfoxide, bis(2,4-dihydroxy-6-methylphenyl)sulfoxide, bis(5-chloro-2,4-dihydroxyphenyl)sulfoxide, bis(2,5-dihydroxyphenyl)sulfoxide and bis(3,4-dihydroxyphenyl)sulfoxide, etc. One of these may be singly used or two or more of these may be mixedly used.

The amides include N,N-dimethylformamide, N,N-dimethylacetamide, oleic amide, stearic acid amide, etc. One of these may be singly used or two or more of these may be mixedly used.

The amines include ammonia, aniline, dimethylamine, triethylamine, ethanolamine, diethylethanolamine, etc. One of these may be singly used or two or more of these may be mixedly used.

The aromatic compounds include benzene, toluene, xylene, phenol, p-cresol, o-cresol, catechins, terpenes, etc. One of these may be singly used or two or more of these may be mixedly used.

The morpholines include N-methylmorpholine, N-methylmorpholine-N-oxide, etc. One of these may be singly used or two or more of these may be mixedly used.

The low-molecular weight compounds include an ionic liquid. As used herein, an ionic liquid refers to a salt which is present in liquid even at room temperature.

Such ionic liquids as described above include 1-butyl-3-methylimidazolium chloride, 1-butyl-3-methylimidazolium, 1-ethyl-3-(hydroxymethyl)pyridinium ethyl sulfate, 1-ethyl-3-methylpyridinium ethyl sulfate, 1.3-dimethyl imidazolium dimethyl phosphate, etc. One of these may be singly used or two or more of these may be mixedly used.

The high-molecular weight compound is at least one selected from the group consisting of alcoholic polymers, ether polymers, amide polymers, amine polymers and aromatic polymers.

The alcoholic polymers include polyethylene glycol, polyetherpolyol, polyesterpolyol, polyvinyl alcohol, amylose, amylopectin, sorbitol, polycaprolactone, polyvalerolactone, polybutyrolactone, polyglycol, polylactic acid, etc. One of these may be singly used or two or more of these may be mixedly used.

The ether polymers include crown ether, polyethylene glycol, polypropylene glycol, etc. One of these may be singly used or two or more of these may be mixedly used.

The amide polymers include polyacrylamide, chitin, chitosan, polyvinylpyrrolidone, polycaprolactam, etc. One of these may be singly used or two or more of these may be mixedly used.

The amine polymers include polyallylamine, polylysine, various amine-modified acrylic copolymers, etc. One of these may be singly used or two or more of these may be mixedly used.

The aromatic polymers include polyphenylene oxide, catechin, tannin, terpene, etc. One of these may be singly used or two or more of these may be mixedly used.

The fatty acid is preferably at least one selected from the group consisting of saturated fatty acids, unsaturated fatty acids and salts thereof.

The saturated fat acids include formic acid, acetic acid, oxalic acid, citric acid, malonic acid, succinic acid, propionic acid, butyric acid, palmitic acid, stearic acid, etc. One of these may be singly used or two or more of these may be mixedly used.

The unsaturated fatty acids include benzoic acid, oleic acid, linoleic acid, linolenic acid, etc. One of these may be singly used or two or more of these may be mixedly used.

The inorganic alkalis include lithium hydroxide, sodium hydroxide, potassium hydroxide, etc. One of these may be singly used or two or more of these may be mixedly used.

The above-mentioned fibrillation material may be a solid or a liquid at room temperature. When it is a solid at room temperature, the fibrillation material preferably becomes a liquid under a temperature condition during mechanical pulverization described below.

In other words, the fibrillation material preferably has a lower melting point than temperature during the mechanical pulverization described below.

In this case, the fibrillation material enters between the microfibrils of cellulose of a cellulosic material, and therefore the entanglement of lignin with cellulose and hemicellulose can be sufficiently undone.

As a mixing rate of a fibrillation material to a cellulosic material, the fibrillation material is preferably 0.01-200 parts by mass, more preferably 0.01-100 parts by mass, further more preferably 0.1-20 parts by mass, with respect to 1 part by mass of the cellulosic material.

When the mixing rate of the fibrillation material is less than 0.01 parts by mass, the cellulosic material tends not to be sufficiently fibrillated in comparison with the case in which the mixing rate is within the above-mentioned range; and when the mixing rate is more than 200 parts by mass, most of the pulverization energy is absorbed in a fibrillation material, the rate of the pulverization energy used in the fibrillation of the cellulosic material is decreased, and the fibrillation tends to be inhibited from efficiently proceeding, in comparison with the case in which the mixing rate is within the above-mentioned range.

When a fibrillation material is constituted of water and a medium of a low-molecular weight compound, a high-molecular weight compound, a fatty acid or inorganic acid, a mixing rate of the medium is preferably 0.1-99.9 mass %, more preferably 0.1-50 mass %, with respect to the total weight of the fibrillation material.

When a fibrillation material is constituted of water and a low-molecular weight compound, a mixing rate of the low-molecular weight compound of 0.1-99.9 mass % with respect to the total weight of the fibrillation material results in entering of a low-molecular weight compound as well as water molecules between tissues or cell walls to swell the tissues.

In addition, there is such an advantage that they enter between cellulose microfibrils by pulverization energy due to mechanical pulverization to facilitate fibrillation by synergistic effect.

When a fibrillation material is constituted of water and a high-molecular weight compound, there is such an advantage that a mixing rate of the high-molecular weight compound of 0.1-99.9 mass % with respect to the total weight of the fibrillation material results in increase of the flexibility of high-molecular weight compound molecules which is enhanced by a swelling effect and a fibrillation effect by water molecules as well as dissolution in water, the high-molecular weight compound having a hydration structure results in facilitation of entering between the gaps of cellulose and hemicellulose having a high affinity for water, and therefore the proceeding of fibrillation is facilitated by synergistic effect.

When a fibrillation material is constituted of water and a fatty acid, a mixing rate of the fatty acid of 0.1-99.9 mass % with respect to the total weight of the fibrillation material results in a swelling effect and a fibrillation effect by water molecules, a lower fatty acid enters between tissues or cell walls like water, and the proceeding of fibrillation is facilitated by synergistic effect.

In addition, a higher fatty acid has such an advantage that the proceeding of fibrillation is facilitated by synergistic effect since the dissolution of the higher fatty acid in water results in the adhesion of water molecules to the periphery of its molecules to become in a hydration state and it is easy to enter between the gaps of cellulose or hemicellulose having a affinity for water.

When a fibrillation material is constituted of water and an inorganic alkali, there is such an advantage that, since an added medium is alkaline, cellulose and hemicellulose in a cellulosic material are hydrolyzed partially, rigid cell walls are embrittled, and a tissue is easily damaged by pulverization energy to facilitate the proceeding of fibrillation.

In addition, alkali ions have a hydration structure and therefore have such an advantage that they enter between tissues and cell walls to widen the network of cellulose and hemicellulose and the proceeding of fibrillation is facilitated by synergistic effect.

Furthermore, depending on the alkali concentration, the crystal structure of cellulose is known to be converted from a cellulose I type crystal to a cellulose II type crystal in a natural type alkali medium. Such an alkali treatment is referred to as a mercerization treatment. The cellulose II type crystal has a high chemical and biological reactivity and facilitates the proceeding of hydrolysis.

Methods of the mechanical pulverization are not limited in particular, but a method capable of coexistence with a medium to apply shearing force to a cellulosic material is preferred. The methods include, for example, methods by a ball mill, a rod mill, a hammer mill, an impeller mill, a high-speed mixer, a disk mill (batch-type or continuous-type), a mixer, a high-pressure homogenizer, a mechanical homogenizer or an ultrasonic wave homogenizer, etc.

Of these, the mechanical pulverization method is carried out preferably by the ball mill, the rod mill, a bead mill, the disk mill or the mixer, more preferably by the ball mill, the disk mill or the mixer.

In this case, a fine fibrous cellulosic material can be comparatively easily produced. In addition, variations in the size of the obtained fine fibrous cellulosic material are reduced.

Particularly preferably, the mechanical pulverization method is carried out by the disk mill.

In this case, there is such advantages that the thick bundle of a cellulosic material in which cellulose microfibrils are assembled may be undone to a thinner cellulosic material by applying pressure or shearing force and this treatment may be continuously carried out.

Pulverization treatment may be also carried out while heating, and a throughput may be also increased by increasing the diameter of the disk.

Mechanical pulverization is performed preferably by a batch-type or continuous-type extruder.

In this case, a fine fibrous cellulosic material can be efficiently produced in a shorter time.

Of these, it is preferable to perform the mechanical pulverization by a twin-screw extruder.

The twin-screw extruder extrudes a material between screws while applying shearing force or pressure thereto, allowing continuous treatment. Therefore, the homogeneous dispersion and penetration of a fibrillation material in an overall cellulosic material is facilitated, and consequently a cellulosic material can be sufficiently fibrillated even with a small amount of fibrillation material.

In addition, the twin-screw extruder enables treatment while heating and therefore comparatively easily uses a molten thermoplastic polymer or the like as a fibrillation material. In this case, since the viscosity after melting becomes high, a strong pressure or shearing force can be propagated and applied to an overall cellulosic material, and the cellulosic material can be fibrillated even with a small amount of fibrillation material.

In addition, when mechanical pulverization is carried out under a high pressure, a blasting effect by pressure relief in a stroke in an outlet is obtained to allow more effective fibrillation.

Mechanical pulverization is preferably performed under a temperature condition of 20-350° C.

When the temperature is lower than 20° C., when using a small amount of fibrillation material, it is not dispersed or penetrated homogeneously into an overall cellulosic material, and the cellulosic material tends not to be sufficiently fibrillated in comparison with the case in which temperature is within the above-mentioned range; and when the temperature is higher than 350° C., the thermal decomposition of the cellulosic material or its modification by oxidation may occur in comparison with the case in which the temperature is within the above-mentioned range.

Mechanical pulverization is preferably carried out under a pressure condition of 0.1-20 MPa.

When the pressure is less than 1 MPa, when adding a low-boiling fibrillation material, a fibrillation material is partially vaporized to inhibit pulverization energy transfer, and therefore a cellulosic material tends not to be fully fibrillated, in comparison with the case in which the pressure is within the above-mentioned range; and when the pressure is more than 20 MPa, a cellulosic material or a fibrillation material may be decomposed or modified in comparison with the case in which the pressure is within the above-mentioned range.

Mechanical pulverization is more preferably carried out under a temperature condition of 20-350° C. and/or a pressure condition of 0.1-20 MPa.

In this case, a fine fibrous cellulosic material can be efficiently produced in a shorter time.

In the mechanical pulverization, pulverization of a cellulosic material with a fibrillation material by mechanically applying shearing force or pressure results in fibrillation of the cellulosic material into cellulose microfibrils.

In this case, when an aspect ratio of the cellulose microfibrils is high, the fibrillation material (medium) is taken between the microfibrils of cellulose, and the viscosity tends to become high.

In this case, it is preferable to preliminarily pulverize (hereinafter referred to as "preliminary pulverization") a cellulosic material to make a chip-like, fibrous or powdered fine cellulosic material.

Then, a slurry fine fibrous cellulosic material having a low aspect ratio is obtained.

Such a fine fibrous cellulosic material has a high flowability, is easy to transport with a pump, and is thus excellent in handleability.

In addition, high flowability facilitates the proceeding of hydrolysis.

In addition, mixing with a fibrillation material and mechanical pulverization are carried out to make a fine fibrous cellulosic material having a width of 1 μm or less and a length of 5,000 μm or less.

In accordance with the production process of fine fibrous cellulose, a fine fibrous cellulosic material can be efficiently produced in a shorter time.

The process for producing a fine fibrous cellulosic material provides a fine fibrous cellulosic material which is fibrillated into a cellulose microfibril in the pure form that is most efficient for a hydrolysis reaction while a cellulosic material is in a solid state without inhibiting the hydrolysis reaction.

In the process for producing a fine fibrous cellulosic material, the unique crystallinity of a cellulosic material is maintained in the obtained fine fibrous cellulosic material since the bundle of the cellulosic material formed by assembling cellulose microfibrils is undone to form the individual cellulose microfibrils. In other words, surface or internal cellulose molecules provide the cellulose microfibrils having crystallinity which are scarcely subjected to the disorder of the sequence and orientation of molecular chains or chemical modification.

Accordingly, the process for producing a fine fibrous cellulosic material provides the fine fibrous cellulosic material, of which the hydrolysis reaction easily proceeds, even in the case of cellulose having a high crystallinity. Particularly, when the hydrolysis is enzymatic hydrolysis, the surface of the cellulose microfibrils is not subjected to strong modification, and therefore the hydrolysis easily proceeds without inhibiting the substrate specificity of an enzyme.

Furthermore, in the process for producing a fine fibrous cellulosic material, an obtained fine fibrous cellulosic material need not be hydrolyzed under severe conditions such as strong chemical agents such as sulfuric acid and high-pressure and high-temperature water since a cellulosic material is a fibrillated cellulose microfibril.

Therefore, the reaction control is easy, and a saccharide can be efficiently produced from the fine fibrous cellulosic material without generating an excessively decomposed product and without applying great pulverization energy.

Fine fibrous cellulose obtained in such a manner can be used not only in the production of a saccharide or ethanol from the saccharide but also as a high-strength material by conjugating as a filler to a resin or the like because of having extremely high strength in terms of a molecular structure.

The fine fibrous cellulose can be also converted into a high-strength material without being processed, without any operation such as the use of an adhesive or the chemical denaturalization of the fine fibrous cellulose, because of having strong self-cohesive power.

In addition, since the fine fibrous cellulose is a natural product, has neither taste nor odor, is atoxic, has fine fibers and therefore offers no foreign body feeling on the tongue, the fine fibrous cellulose can be added to a food product to be imparted with water retentivity, oil retentivity, texture, morphological stability or dietetic properties.

A process for producing a saccharide from the above-mentioned fine fibrous cellulose will be described below.

A saccharide is obtained by hydrolyzing the fine fibrous cellulose.

Hydrolysis methods include acid hydrolysis using acids such as sulfuric acid, hydrochloric acid and fluorinated acid and enzymatic hydrolysis using enzymes such as cellulases.

Of these, the hydrolysis is preferably enzymatic hydrolysis.

In this case, a cellulosic material can be sufficiently hydrolyzed with a comparatively small amount of enzyme, and therefore a saccharide can be inexpensively obtained.

In the enzymatic hydrolysis, no side reaction occurs, and no excessively decomposed product is generated.

The cellulases are classified roughly into endo-type and exo-type cellulases. The endo-type cellulases well hydrolyze amorphous cellulose, whereas the exo-type cellulases well hydrolyze crystalline cellulose.

Accordingly, when a fine fibrous cellulosic material is hydrolyzed, the effects of these enzymes are synergistically shown by using the mixture of the endo-type and exo-type cellulases.

In case of the enzymatic hydrolysis, when any material which inhibits an enzyme reaction or deactivates an enzyme is not contained in a mixture of fine fibrous cellulose obtained during the step of producing the above-mentioned fine fibrous cellulose and a fibrillation material, the mixture may be mixed with an enzyme without being processed to perform hydrolysis.

In contrast, when a material which inhibits an enzyme reaction or deactivates an enzyme is contained in the mixture, the mixture may be diluted till the effect of the material is deteriorated, followed by the enzymatic hydrolysis. The (inhibition) material may be also removed by washing, solvent substitution, decompression or the like, followed by the enzymatic hydrolysis.

Saccharides are obtained in such a manner. Further, glucose is obtained from cellulose; and xylose, mannose, arabinose, galactose and the like are obtained from hemicellulose.

Saccharified solutions from these saccharides (solutions in which the saccharides are dissolved in water or a buffer to be prepared at pH facilitating the action of yeast fungi) can be converted into ethanol by fermentation.

The ethanol is used in raw materials for chemical products, solvents, automotive fuels, etc. An aqueous solution containing the ethanol may be also made to be an alcoholic beverage.

The saccharified solutions are also used as medium materials or carbon sources for biologically producing useful resources.

The saccharified solutions are also used in useful materials such as chemical products, polymer raw materials and physiologically active materials by chemically converting the saccharides.

The preferred embodiment of the present invention was described above, but the present invention is not limited to the embodiment.

For example, the fine fibrous cellulosic material according to the present embodiment need not be derived from a plant.

Specifically, it may be a fine fibrous cellulosic material derived from ascidian, acetic acid bacteria and the like.

In the production process of a fine fibrous cellulosic material, it is preferable to immerse a cellulosic material in an aqueous inorganic alkaline solution for several hours to several days prior to mechanical pulverization.

In this case, the cellulosic material is prone to be undone by swelling, and cellulose and hemicellulose are hydrolyzed to decrease a molecular weight.

As a result, the cellulosic material is embrittled. In other words, cellulose microfibrils are partially cut or prone to be cut by external force.

Then, the fibrillation of the cellulosic material promptly proceeds, resulting in improvement in hydrolyzability. A fine fibrous cellulosic material to be obtained is shortened and has an enhanced flowability.

As used herein, inorganic alkalis as described above include lithium hydroxide, sodium hydroxide, potassium hydroxide and the like.

In the production process of a fine fibrous cellulosic material, it is preferable to perform hydrothermal treatment of a cellulosic material using an autoclave and the like prior to mechanical pulverization.

In this case, the cellulosic material is prone to be undone by swelling, and cellulose and hemicellulose are hydrolyzed to decrease a molecular weight.

As a result, the cellulosic material is embrittled. In other words, cellulose microfibrils are partially cut or prone to be cut by external force.

Then, the fibrillation of the cellulosic material promptly proceeds, resulting in improvement in hydrolyzability. A fine fibrous cellulosic material to be obtained is shortened and has an enhanced flowability.

In the production process of a fine fibrous cellulosic material, it is preferable to carry out mechanical pulverization, followed by adding water, ethanol and/or acetic acid and performing heat treatment.

In this case, hydrolyzability is significantly improved by the partial dissolution and desorption of hemicellulose and lignin.

Although a fine fibrous cellulosic material is produced and then hydrolyzed in the process for producing a saccharide of the above-mentioned embodiment, the fine fibrous cellulosic material may be hydrolyzed concurrently with being produced.

Specifically, an enzyme is mixed with a cellulosic material containing cellulose, hemicellulose and lignin and a fibrillation material for fibrillating the cellulosic material, and a saccharide can be obtained from a cellulosic material in a high yield at a time by mechanical pulverization.

In such a process, hemicellulose and lignin are removed by the fine fiberization of the cellulosic material, cellulose microfibrils appear on a surface, and the enzyme approaches and is adsorbed to the cellulose microfibrils to hydrolyze the fine fibrous cellulosic material.

In addition, new gaps are formed in the cellulose microfibrils by the hydrolysis, a fibrillation material enters thereinto, and fibrillation further proceeds. As described above, in accordance with the production process of a saccharide, fibrillation and enzymatic hydrolysis are simultaneously carried out to produce a mutual synergistic effect.

EXAMPLES

Examples of the fine fibrous cellulosic material of the present invention will be specifically described below, but the present invention is not limited thereto.

Example 1

An example using a eucalyptus which is a broad-leaved tree as a raw material for a cellulosic material and a planetary ball mill for mechanical pulverization is shown.

The rough pulverization of eucalyptus chips for making paper was performed to make 0.2 mm-pass eucalyptus wood flour by a cutter mill. The resultant eucalyptus wood flour (20 g) was charged into a planetary ball mill pot made of zirconia (internal capacity: 500 ml; P-5 type; manufactured by Fritsch Corporation (Germany)), and 25 zirconia balls having a diameter of 20 mm were filled thereinto.

Subsequently, 200 ml of water (fibrillation material) was added as a medium (eucalyptus wood flour in ten times the amount of water), and a lid was put on the planetary ball mill pot made of zirconia. In ball mill treatment, a cycle of treatment at an autorotation speed of 120 rpm for 20 minutes and stop for 10 minutes was repeated 100 times, and mechanical pulverization (hereinafter also referred to as "fibrillation treatment") was performed for a total treatment time of 33 hours to obtain a brown, creamy mixture. As the conditions of the fibrillation treatment, temperature and pulverization energy (gravitational acceleration) which can be applied to the ball in the container of the ball mill were set at 40° C. and 1.8 G at 120 rpm, respectively.

The water in the mixture was substituted with t-butylalcohol, and a dried sample 1 (fine fibrous cellulosic material; average width of 0.07 μm and average length of 4 μm) was obtained by drying under reduced pressure. The aspect ratio of the sample 1 was measured from an SEM observation image.

Example 2

A sample 2 (fine fibrous cellulosic material; average width of 0.04 μm and average length of 7 μm) was obtained by the same method as in Example 1 except that eucalyptus wood flour was 13.5 g. The amount of water was 15 times that of the eucalyptus wood flour. As a result of fibrillation treatment, the obtained mixture had low viscosity and was brown and a slurry.

Comparative Example 1

The rough pulverization of eucalyptus chips for making paper used as the eucalyptus was performed to make 0.2 mm-pass eucalyptus wood flour by the cutter mill, and a sample A (cellulosic material; average width of 50 μm and average length of 250 μm) was obtained. No fibrillation treatment was carried out.

[Evaluation 1, Particle Size Distribution]

The samples 1 and 2 (100 mg) were dispersed in 30 ml of water, respectively, followed by measuring a particle size distribution by an aqueous medium circulation cell in a laser diffraction type particle size distribution measuring apparatus (Model LMS-24; manufactured by Seishin Corporation).

The obtained measurement results are listed in Table 1. The values listed in Table 1 exhibit the sizes of the light aggregates of the fine fibrous cellulosic materials.

TABLE 1

|  | Mean particle diameter |
|---|---|
| Example 1 | 8.4 μm |
| Example 2 | 6.2 μm |

It was clear from the results in Table 1 that the mean particle diameter was decreased with decreasing the rate of the water to the eucalyptus wood flour.

Evaluation 2, Microscopy

Scanning electron microscopy was performed to examine the geometry of the sample 2.

An extremely small amount of sample 2 was put on the sample table of the scanning electron microscope made of aluminum using a double-stick tape, and surface electroconductive treatment was performed by platinum vapor deposition, followed by observation by a scanning electron microscope (S-3400 Model; manufactured by Hitachi High-Technologies Corporation) at an acceleration voltage of 25 kV.

The electron microscope photograph of the observation result of the obtained sample 2 is shown in FIG. 1.

As shown in FIG. 1, the fibrous cellulose of from around 100 nm to around 10 nm in the fine part was able to be observed. Further, the observation result of the sample 1 obtained in Example 1 was also similar (not shown).

Evaluation 3, Crystallinity

The crystallinities of the sample 2 and the sample A were evaluated by powder X-ray diffractometry. Specifically, 100 mg of sample 2 and sample A were formed as discoid pellets in a die having a diameter of 13 mm, respectively, and the diffraction patterns were measured with CuKα radiation at 50 kV-300 mA using a RINT-TTR3 type powder X-ray diffraction apparatus (manufactured by Rigaku Corporation).

Figure 2:
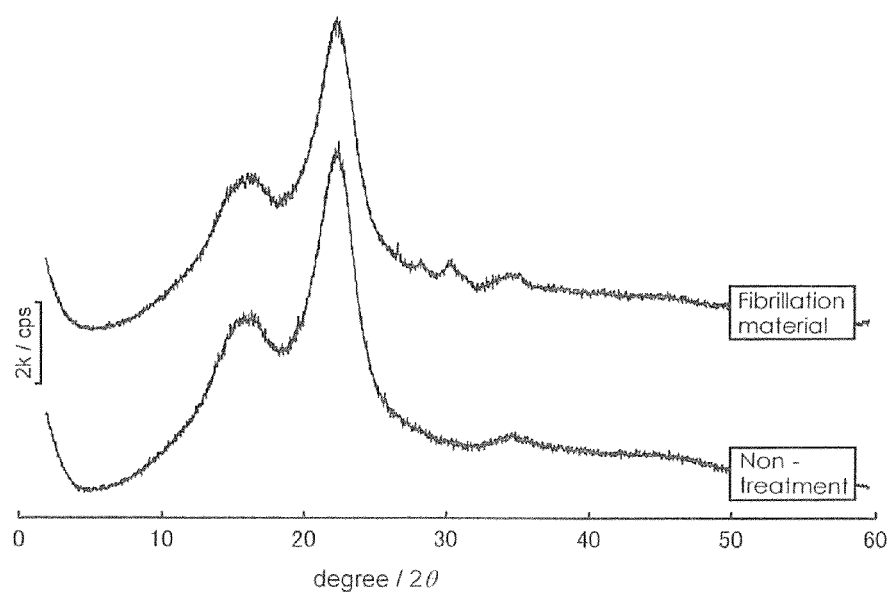
FIG. 2 is a graph illustrating diffraction patterns prepared by measuring the crystallinities of the sample 2 obtained in Example 2 and the sample A obtained in Comparative Example 1 by powder X-ray diffractometry.

The obtained results of the measurement are shown in FIG. 2. Generally, in wood such as eucalyptus and many plant bodies, only cellulose ingredients have crystallinity and give diffraction peaks; however, since hemicellulose and lignin are amorphous, they give halo patterns having peaks at about 20 degrees.

As shown in FIG. 2, the crystallinity of the sample 2 was same as that of the sample A, indicating almost no change in crystallinity. In the sample 1, the observation results (not shown) were similar.

From this, the fibrillation was considered to be good in the sample 1 and the sample 2.

Evaluation 4, Hydrolysis

The enzymatic hydrolysis was carried out using the samples 1, 2 and A. Specifically, the samples 1, 2 and A (50 mg) were suspended in 15 ml of acetate buffer (pH 5.0, 50 mM), respectively. To the suspension was added 2 ml of enzyme solution (enzyme level: 2 mg) prepared by dissolving 50 mg of meicelase (enzyme; manufactured by Meiji Seika Kaisha, Ltd.) in 50 ml of acetate buffer (pH 5.0) to make enzymatic hydrolysis test liquids 1, 2 and A, of which the total amount was 17 ml. Further, the test liquids were set in a dry incubator at 45° C. just after the addition of the enzyme liquid, and the enzymatic hydrolysis was made to proceed at 120 rpm.

In addition, 200 μL was taken out of the enzymatic hydrolysis test liquids 1, 2 and A at evenly spaced time intervals (time is listed in Table 2), the supernatants after centrifugation were colored by Glucose Test Wako (manufactured by Wako Pure Chemical Industries, Ltd.), and the absorbances were measured using a spectrophotometer. Glucose concentrations were calculated, based on a previously prepared calibration curve, from the obtained absorbances. Further, the glucose concentrations are shown as values on a 50 mg solid basis.

The glucose concentrations obtained from the samples 1, 2 and A are listed in Table 2. The amounts of glucoses dissolved when suspending the samples in the acetate buffer prior to the charge of the enzyme are shown at enzyme reaction time of 0 hour. The total saccharide concentrations of the samples 1, 2 and A, determined by a phenol-sulfuric acid method, are listed in Table 3.

TABLE 2

| Enzyme | Glucose concentration (mg/L) | | |
|---|---|---|---|
| reaction time (hr) | Example 1 (Sample 1) | Example 2 (Sample 2) | Comparative Example 1 (Sample A) |
| 0 | 6.9 | 4.9 | 8.5 |
| 1 | 258.8 | 211.4 | 45.8 |
| 3 | 402.4 | 337.1 | 48.7 |
| 6 | 444.6 | 399.2 | 52.7 |
| 12 | 512.4 | 425.1 | 54.4 |
| 18 | 481.5 | 455.6 | 58.8 |
| 24 | 466.9 | 466.5 | 59.6 |
| 36 | 485.6 | 454.8 | 60.0 |
| 48 | 501.8 | 472.2 | 60.9 |

TABLE 3

| Enzyme | Total saccharide concentration (mg/L) | | |
|---|---|---|---|
| reaction time (hr) | Example 1 (Sample 1) | Example 2 (Sample 2) | Comparative Example 1 (Sample A) |
| 0 | 254.5 | 269.7 | 245.2 |
| 48 | 908.6 | 862.5 | 371.2 |

It was clear from the results of Table 2 that the glucose concentrations of the samples 1 and 2 were about ten times as high as that of the sample A.

This is possibly because the enzymatic hydrolysis of the celluloses of the samples 1 and 2 proceeds (indicating the proceeding of the enzymatic hydrolysis). Since an enzyme hydrolyzing hemicellulose was included in the enzymes used and hemicellulose is more easily hydrolyzed than cellulose, the hydrolysis of hemicellulose is more likely to also concurrently proceed when a glucose concentration is high.

It was clear from the results of Table 3 that, with regard to total saccharide concentration after 48 hours, the glucose concentrations of the samples 1 and 2 were about twice as high as that of the sample A.

This indicated that the hydrolysis of hemicellulose as well as cellulose proceeded.

Example 3

An example of using chips for making paper, of Oregon pine which is an acicular tree, as a raw material for a cellulosic material, and using a planetary ball mill for mechanical pulverization is shown.

The rough pulverization of the Oregon pine chips for making paper was performed to make 0.2 mm-pass Oregon pine wood flour by a cutter mill. The resultant Oregon pine wood flour (2.3 g) was charged into a planetary ball mill pot made of zirconia (internal capacity: 45 ml; P-7 type; manufactured by Fritsch Corporation (Germany)), and seven zirconia balls having a diameter of 10 mm were filled thereinto.

Subsequently, 23 ml of water (fibrillation material) was added as a medium (Oregon pine wood flour in ten times the amount of water), and a lid was put on the planetary ball mill pot made of zirconia. In ball mill treatment, a cycle of treatment at an autorotation speed of 200 rpm for 20 minutes and stop for 10 minutes was repeated 100 times, and fibrillation treatment was performed for total treatment time of 33 hours to obtain a milky-white, creamy mixture. As the conditions of the fibrillation treatment, temperature and pulverization energy which can be applied to the ball in the container of the ball mill were set at 40° C. and 1.8 G, respectively.

The water in the mixture was substituted with t-butylalcohol, and a dried sample 3 (fine fibrous cellulosic material; average width of 0.05 μm and average length of 15 μm) was obtained by drying under reduced pressure.

Example 4

A sample 4 (fine fibrous cellulosic material; average width of 0.07 μm and average length of 10 μm) was obtained by the same method as in Example 3 except that Oregon pine wood flour was 3.3 g. The amount of water was 7 times that of the Oregon pine wood flour. As a result of fibrillation treatment, the obtained mixture was milky-white and creamy.

Comparative Example 2

The rough pulverization of Oregon pine chips for making paper was performed to make 0.2 mm-pass Oregon pine wood flour by the cutter mill, and a sample B (cellulosic material; average width of 50 μm and average length of 250 μm) was obtained. No fibrillation treatment was carried out.

Evaluation 5, Particle Size Distribution

Particle size distributions were measured by the same method as in Evaluation 1 except that the samples 3 and 4 were used instead of the samples 1 and 2.

The obtained measurement results are listed in Table 4.

TABLE 4

| | Mean particle diameter |
|---|---|
| Example 3 | 7.4 μm |
| Example 4 | 10.5 μm |

Evaluation 6, Microscopy

Scanning electron microscopy was performed by the same method as in Evaluation 2 except that the sample 4 was used instead of the sample 2.

Figure 3:
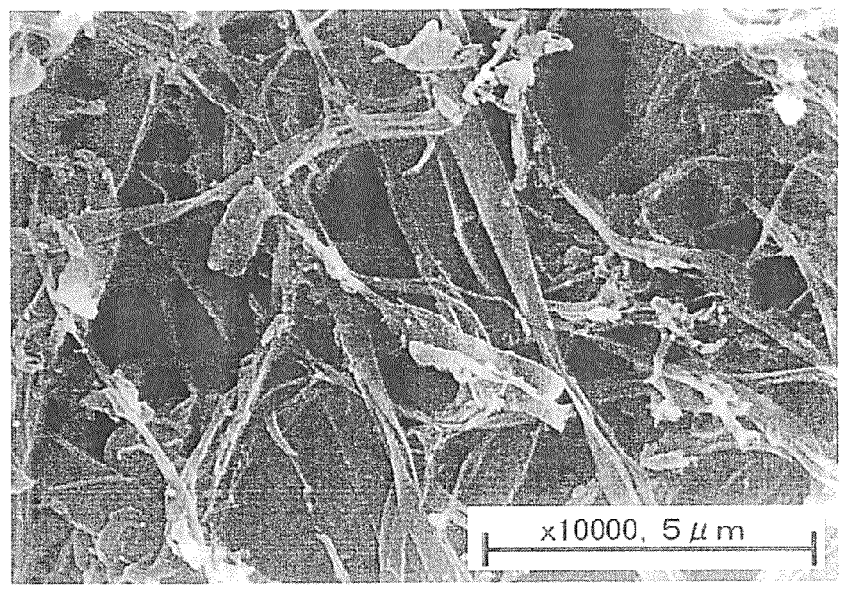
FIG. 3 is a scanning electron micrograph of a sample 4 obtained in Example 4.

The electron microscope photograph of the observation result of the obtained sample 4 is shown in FIG. 3.

As shown in FIG. 3, the fibrous cellulose of from around 100 nm to around 10 nm in the fine part was able to be observed. Further, the observation result of the sample 3 obtained in Example 3 was also similar (not shown).

Evaluation 7, Hydrolysis

Glucose concentrations were calculated by the same method as in Evaluation 4 except that the samples 3, 4 and B were used instead of the samples 1, 2 and A.

The glucose concentrations obtained from the samples 3, 4 and B are listed in Table 5. The amounts of glucoses dissolved when suspending the samples in the acetate buffer prior to the charge of the enzyme are shown at enzyme reaction time of 0 hour. The total saccharide concentrations of the samples 3, 4 and B, determined by a phenol-sulfuric acid method, are listed in Table 6.

TABLE 5

| | Glucose concentration (mg/L) | | |
|---|---|---|---|
| Enzyme reaction time (hr) | Example 3 (Sample 3) | Example 4 (Sample 4) | Comparative Example 2 (Sample B) |
| 0 | 4.5 | 2.8 | 3.7 |
| 1 | 162.7 | 136.3 | 58.0 |
| 3 | 289.6 | 195.1 | 81.5 |
| 6 | 370.4 | 256.0 | 102.6 |
| 12 | 466.1 | 301.0 | 126.6 |
| 18 | 482.3 | 329.8 | 133.1 |
| 24 | 487.6 | 342.4 | 142.0 |
| 36 | 564.7 | 380.1 | 157.8 |
| 48 | 593.9 | 377.3 | 163.5 |

TABLE 6

| | Total saccharide concentration (mg/L) | | |
|---|---|---|---|
| Enzyme reaction time (hr) | Example 3 (Sample 3) | Example 4 (Sample 4) | Comparative Example 2 (Sample B) |
| 0 | 212.1 | 253.7 | 265.7 |
| 48 | 1159.0 | 880.0 | 549.2 |

It was clear from the results of Table 5 that the glucose concentrations of the samples 3 and 4 were about twice to four times as high as that of the sample B.

This is possibly because the enzymatic hydrolysis of the celluloses of the samples 3 and 4 proceeds (indicating the proceeding of the enzymatic hydrolysis). Since hemicellulose is more easily hydrolyzed than cellulose, the hydrolysis of hemicellulose is more likely to also concurrently proceed when a glucose concentration is high.

It was clear from the results of Table 6 that, with regard to total saccharide concentration after 48 hours, the glucose concentrations of the samples 3 and 4 were about 1.5-2 times as high as that of the sample B. This indicated that the hydrolysis of hemicellulose as well as cellulose proceeded.

Example 5

The rough pulverization of the Oregon pine chips for making paper was performed to make 2 mm-pass Oregon pine wood flour by a cutter mill. The resultant Oregon pine wood flour (13.5 g) was charged into a planetary ball mill pot made of zirconia (internal capacity: 500 ml; manufactured by Fritsch Corporation (Germany)), and 25 zirconia balls having a diameter of 20 mm were filled thereinto.

Subsequently, 200 ml of water (fibrillation material) was added as a medium, and a lid was put on the planetary ball mill pot made of zirconia. In ball mill treatment, a cycle of treatment at an autorotation speed of 120 rpm for 20 minutes and stop for 10 minutes was repeated 100 times, and fibrillation treatment was performed for total treatment time of 33 hours to obtain a milky-white, creamy mixture. As the conditions of the fibrillation treatment, temperature and pulverization energy which can be applied to the ball in the container of the ball mill were set at 40° C. and 1.8 G at 120 rpm, respectively.

The water in the mixture was substituted with t-butylalcohol, and a dried sample 5 (fine fibrous cellulosic material; average width of 0.08 μm and average length of 10 μm) was obtained by drying under reduced pressure.

Comparative Example 3

The rough pulverization using Oregon pine chips for making paper was performed to make 2 mm-pass Oregon pine wood flour by the cutter mill, and a sample C (cellulosic material; average width of 1,500 and average length of 3,500 μm) was obtained. No fibrillation treatment was carried out.
Evaluation 8, Hydrolysis Glucose concentrations were calculated by the same method as in Evaluation 4 except that the samples 5 and C were used instead of the samples 1, 2 and A.

The glucose concentrations obtained from the samples 5 and C are listed in Table 7. The amounts of glucoses dissolved when suspending the samples in the acetate buffer prior to the charge of the enzyme are shown at enzyme reaction time of 0 hour.

TABLE 7

| | Glucose concentration (mg/L) | |
|---|---|---|
| Enzyme reaction time (hr) | Example 5 (Sample 5) | Comparative Example 3 (Sample C) |
| 0 | 7.3 | 2.6 |
| 48 | 866.1 | 103.5 |

It was clear from the results of Table 7 that the glucose concentration of the samples 5 was about eight times as high as that of the sample C.

This is possibly because the enzymatic hydrolysis of the celluloses of the sample 5 proceeds (indicating the proceeding of the enzymatic hydrolysis). Since hemicellulose is more easily hydrolyzed than cellulose, the hydrolysis of hemicellulose is more likely to also concurrently proceed when a glucose concentration is high.

Example 6

The rough pulverization of the Oregon pine chips for making paper was performed to make 0.2 mm-pass Oregon pine wood flour by a cutter mill. The resultant Oregon pine wood flour (2.0 g) was charged into a planetary ball mill pot made of zirconia (internal capacity: 45 ml; manufactured by Fritsch Corporation (Germany)), and seven zirconia balls having a diameter of 10 mm were filled thereinto.

Subsequently, water (fibrillation material) was added as a medium to be 20 mass % with respect to the total amount, and a lid was put on the planetary ball mill pot made of zirconia. In ball mill treatment, a cycle of treatment at an autorotation speed of 400 rpm for 20 minutes and stop for 10 minutes was repeated six times, and fibrillation treatment was performed for a total treatment time of 2 hours to obtain a pale yellow powdered mixture. As the conditions of the fibrillation treatment, temperature and pulverization energy which can be applied to the ball in the container of the ball mill were set at 40° C. and 7.8 G at 400 rpm, respectively.

The water in the mixture was substituted with t-butylalcohol, and a dried sample 6 having a low aspect ratio (fine fibrous cellulosic material; average width of 0.9 μm and average length of 3 μm) was obtained by drying under reduced pressure.

Example 7

A sample 7 (fine fibrous cellulosic material; average width of 0.8 μm and average length of 5 μm) was obtained by the same method as in Example 6 except that acetic acid (fibrillation material) was used instead of water.

Example 8

A sample 8 having a low aspect ratio (fine fibrous cellulosic material; average width of 0.9 μm and average length of 5 μm) was obtained by the same method as in Example 6 except that polyethylene glycol 400 (molecular weight: 400; PEG 400) (fibrillation material) was used instead of water.

Example 9

A sample 9 having a low aspect ratio (fine fibrous cellulosic material; average width of 1 μm and average length of 10 μm) was obtained by the same method as in Example 6 except that 1,4-dioxane (fibrillation material) was used instead of water.

Example 10

A sample 10 having a low aspect ratio (fine fibrous cellulosic material; average width of 1 μm and average length of 3 μm) was obtained by the same method as in Example 6 except that dimethyl sulfoxide (DMSO) (fibrillation material) was used instead of water.

Example 11

A sample 11 (fine fibrous cellulosic material; average width of 1 μm and average length of 3 μm) was obtained by the same method as in Example 6 except that dimethylacetamide (DMAc) (fibrillation material) was used instead of water.

Example 12

A sample 12 (fine fibrous cellulosic material; average width of 0.9 μm and average length of 3 μm) was obtained by the same method as in Example 6 except that ethanol (EtOH) (fibrillation material) was used instead of water.

Evaluation 9, Hydrolysis

Glucose concentrations were calculated by the same method as in Evaluation 4 except that the samples 6 to 12 were used instead of the samples 1, 2 and A.

The glucose concentrations obtained from the samples 6 to 12 are listed in Table 8. The amounts of glucoses dissolved when suspending the samples in the acetate buffer prior to the charge of the enzyme are shown at enzyme reaction time of 0 hour.

TABLE 8

| Enzyme reaction time (hr) | Glucose concentration (mg/L) | | | |
|---|---|---|---|---|
| | Example 6 (Sample 6) | Example 7 (Sample 7) | Example 8 (Sample 8) | Example 9 (Sample 9) |
| 0 | 5.7 | 6.5 | 3.2 | 3.2 |
| 48 | 1043.8 | 966.7 | 614.2 | 639.3 |

| Enzyme reaction time (hr) | Glucose concentration (mg/L) | | |
|---|---|---|---|
| | Example 10 (Sample 10) | Example 11 (Sample 11) | Example 12 (Sample 12) |
| 0 | 2.4 | 4.1 | 7.7 |
| 48 | 770.7 | 676.7 | 655.2 |

It was clear from the results of Table 8 that, in the samples 6 to 12, the amounts of generated glucoses were increased in all the samples although the amounts of the generated glucoses differ according to the fibrillation materials.

Example 13

A sample 13 (fine fibrous cellulosic material; average width of 0.9 μm and average length of 3 μm) was obtained by the same method as in Example 6 except that added water was 30 mass %.

Example 14

A sample 14 (fine fibrous cellulosic material; average width of 1 μm and average length of 2 μm) was obtained by the same method as in Example 6 except 30 mass % of glycerin was used instead of water.

Example 15

A sample 15 (fine fibrous cellulosic material; average width of 0.9 μm and average length of 3 μm) was obtained by the same method as in Example 6 except 30 mass % of ethylene glycol was used instead of water.

Evaluation 10, Hydrolysis

Glucose concentrations were calculated by the same method as in Evaluation 4 except that the samples 13 to 15 were used instead of the samples 1, 2 and A.

The glucose concentrations obtained from the samples 13 to 15 are listed in Table 9. The amounts of glucoses dissolved when suspending the samples in the acetate buffer prior to the charge of the enzyme are shown at enzyme reaction time of 0 hour.

TABLE 9

| Enzyme reaction time (hr) | Glucose concentration (mg/L) | | |
|---|---|---|---|
| | Example 13 (Sample 13) | Example 14 (Sample 14) | Example 15 (Sample 15) |
| 0 | 3.2 | 5.3 | 2.8 |
| 48 | 799.2 | 668.5 | 853.5 |

It was clear from the results of Table 9 that, in the samples 13 to 15, the amounts of generated glucoses were increased in all the samples although the amounts of the generated glucoses differ according to the fibrillation materials.

Example 16

The rough pulverization of the Oregon pine chips for making paper was performed to make 0.2 mm-pass Oregon pine wood flour by a cutter mill. The resultant Oregon pine wood flour (1.5 g) was charged into a planetary ball mill pot made of zirconia (internal capacity: 45 ml; manufactured by Fritsch Corporation (Germany)), and seven zirconia balls having a diameter of 10 mm were filled thereinto.

Subsequently, 23 ml of water (fibrillation material) was added as a medium, and a lid was put on the planetary ball mill pot made of zirconia. In ball mill treatment, a cycle of treatment at an autorotation speed of 400 rpm for 20 minutes and stop for 10 minutes was repeated six times, and fibrillation treatment was performed for total treatment time of 2 hours to obtain a milky-white, creamy mixture. As the conditions of the fibrillation treatment, temperature and pulverization energy which can be applied to the ball in the container of the ball mill were set at 40° C. and 7.8 G at 400 rpm, respectively.

The water in the mixture was substituted with t-butylalcohol, and a dried sample 16 (fine fibrous cellulosic material; average width of 0.05 µm and average length of 7 µm) was obtained by drying under reduced pressure.

Example 17

A sample 17 (fine fibrous cellulosic material; average width of 0.07 µm and average length of 5 µm) was obtained by the same method as in Example 16 except that methanol (MeOH) (fibrillation material) was used instead of water.

Example 18

A sample 18 (fine fibrous cellulosic material; average width of 0.07 µm and average length of 5 µm) was obtained by the same method as in Example 16 except that ethanol (EtOH) (fibrillation material) was used instead of water.

Example 19

A sample 19 (fine fibrous cellulosic material; average width of 0.12 µm and average length of 5 µm) was obtained by the same method as in Example 16 except that 1-propanol (1-PrOH) (fibrillation material) was used instead of water.

Example 20

A sample 20 (fine fibrous cellulosic material; average width of 0.3 µm and average length of 5 µm) was obtained by the same method as in Example 16 except that 2-propanol (2-PrOH) (fibrillation material) was used instead of water.

Example 21

A sample 21 (fine fibrous cellulosic material; average width of 0.3 µm and average length of 2 µm) was obtained by the same method as in Example 16 except that toluene (fibrillation material) was used instead of water.

Evaluation 11, Hydrolysis

Glucose concentrations were calculated by the same method as in Evaluation 4 except that the samples 16 to 21 were used instead of the samples 1, 2 and A.

The glucose concentrations obtained from the samples 16 to 21 are listed in Table 10. The amounts of glucoses dissolved when suspending the samples in the acetate buffer prior to the charge of the enzyme are shown at enzyme reaction time of 0 hour.

TABLE 10

| Enzyme | Glucose concentration (mg/L) | | |
|---|---|---|---|
| reaction time (hr) | Example 16 (Sample 16) | Example 17 (Sample 17) | Example 18 (Sample 18) |
| 0 | 0.0 | 8.1 | 2.0 |
| 48 | 958.2 | 1071.4 | 919.3 |

| Enzyme | Glucose concentration (mg/L) | | |
|---|---|---|---|
| reaction time (hr) | Example 19 (Sample 19) | Example 20 (Sample 20) | Example 21 (Sample 21) |
| 0 | 2.8 | 3.2 | 6.1 |
| 48 | 604.4 | 468.5 | 997.9 |

It was clear from the results of Table 10 that, in the samples 16 to 21, the amounts of generated glucoses were increased in all the samples although the amounts of the generated glucoses differ according to the fibrillation materials.

Example 22

A sample 22 (fine fibrous cellulosic material; average width of 0.15 µm and average length of 10 µm) was obtained by the same method as in Example 16 except that 23 ml of aqueous solution of 20 wt % polyethylene glycol 400 (molecular weight: 400; PEG 400) was used instead of water.

Example 23

A sample 23 (fine fibrous cellulosic material; average width of 0.05 µm and average length of 10 µm) was obtained by the same method as in Example 16 except that 23 ml of aqueous solution of 20 wt % acetic acid was used instead of water.

Example 24

A sample 24 (fine fibrous cellulosic material; average width of 0.2 µm and average length of 20 µm) was obtained by the same method as in Example 16 except that 23 ml of aqueous solution of 20 wt % 1,4-dioxane was used instead of water.

Example 25

A sample 25 (fine fibrous cellulosic material; average width of 0.1 µm and average length of 10 µm) was obtained by the same method as in Example 16 except that 23 ml of aqueous solution of 20 wt % dimethyl sulfoxide (DMSO) was used instead of water.

Evaluation 12, Hydrolysis

Glucose concentrations were calculated by the same method as in Evaluation 4 except that the samples 22 to 25 were used instead of the samples 1, 2 and A.

The total saccharide concentrations of the samples 22 to 25, determined by a phenol-sulfuric acid method, are listed in Table 11.

TABLE 11

| Enzyme | Total saccharide concentration (mg/L) | | | |
|---|---|---|---|---|
| reaction time (hr) | Example 22 (Sample 22) | Example 23 (Sample 23) | Example 24 (Sample 24) | Example 25 (Sample 25) |
| 0 | 218.3 | 245.0 | 242.7 | 275.4 |
| 48 | 606.4 | 674.7 | 626.6 | 613.3 |

It was clear from the results of Table 11 that, in the samples 22 to 25, the amounts of generated glucoses were increased in all the samples although the amounts of the generated glucoses differ according to the fibrillation materials.

Example 26

As a cellulosic material, 1.5 g of purified wood pulp W-100 (manufactured by Nippon Paper Chemicals Co., Ltd.) was charged into a planetary ball mill pot made of zirconia (internal capacity: 45 ml; manufactured by Fritsch Corporation (Germany)), and seven zirconia balls having a diameter of 10 mm were filled thereinto.

Subsequently, 23 ml of water (fibrillation material) was added as a medium, and a lid was put on the planetary ball mill pot made of zirconia. In ball mill treatment, a cycle of treatment at an autorotation speed of 400 rpm for 20 minutes and stop for 10 minutes was repeated six times, and fibrillation treatment was performed for total treatment time of 2 hours to obtain a brown, creamy mixture. As the conditions of the fibrillation treatment, temperature and pulverization energy which can be applied to the ball in the container of the ball mill were set at 40° C. and 7.8 G at 400 rpm, respectively.

The water in the mixture was substituted with t-butylalcohol, and a dried sample 26 (fine fibrous cellulosic material; average width of 0.05 µm and average length of 10 µm) was obtained by drying under reduced pressure. The above-mentioned purified pulp (W-100) was subjected to various types of chemical treatment and pulverization treatment in a production step and therefore fibrillated to some extent.

Example 27

A sample 27 (fine fibrous cellulosic material; average width of 0.1 µm and average length of 7 µm) was obtained by the same method as in Example 26 except that ethanol (EtOH) was used instead of water.

Example 28

A sample 28 (fine fibrous cellulosic material; average width of 0.05 µm and average length of 15 µm) was obtained by the same method as in Example 26 except that CF 11 (manufactured by Whatman) was used instead of W-100.

Example 29

A sample 29 (fine fibrous cellulosic material; average width of 0.1 µm and average length of 10 µm) was obtained by the same method as in Example 28 except that ethanol (EtOH) was used instead of water.

Evaluation 13, Hydrolysis

Glucose concentrations were calculated by the same method as in Evaluation 4 except that the samples 26 to 29 were used instead of the samples 1, 2 and A.

The glucose concentrations obtained from the samples 26 to 29 are listed in Table 12. The amounts of glucoses dissolved when suspending the samples in the acetate buffer prior to the charge of the enzyme are shown at enzyme reaction time of 0 hour.

TABLE 12

| | Glucose concentration (mg/L) | | | |
| --- | --- | --- | --- | --- |
| | W-100 | | CF11 | |
| Enzyme reaction time (hr) | Example 26 (Sample 26) | Example 27 (Sample 27) | Example 28 (Sample 28) | Example 29 (Sample 29) |
| 0 | 6.9 | 3.2 | 4.1 | 14.2 |
| 48 | 2676.6 | 2531.8 | 2995.8 | 2795.1 |

The result of Table 12 reveals that, in the purified wood pulps of the samples 26 and 27 and the purified raw cotton linters of the samples 28 and 29, hemicellulose and lignin were removed during a purification step, a cellulose content was 90% or more, and therefore the amount of generated glucose became twice or more as much as that in the case of using the wood when the enzymatic hydrolysis proceeded.

It was also clear that the amounts of generated glucoses were increased in all the samples although the amounts of the generated glucoses differ according to the fibrillation materials.

Example 30

The rough pulverization of eucalyptus chips for making paper used as cellulosic materials was performed to make 0.2 mm-pass eucalyptus wood flour by a cutter mill. The resultant eucalyptus wood flour (1.5 g) was charged into a planetary ball mill pot made of zirconia (internal capacity: 45 ml; manufactured by Fritsch Corporation (Germany)), and seven zirconia balls having a diameter of 10 mm were filled thereinto.

Subsequently, 23 ml of acetate buffer (pH 5.0; 50 mM) as a medium and 150 mg of meicelase (manufactured by Meiji Seika Kaisha, Ltd.) were added, and a lid was put on the planetary ball mill pot made of zirconia. In ball mill treatment, a cycle of treatment at an autorotation speed of 200 rpm for 20 minutes and stop for 10 minutes was repeated 100 times, and fibrillation treatment was performed for total treatment time of 33 hours to obtain a brown slurry mixture having a comparatively high flowability, a sample 30.

Reference Example 1

A sample D was obtained by the same method as in Example 30 except that no meicelase (enzyme) was used.

Example 31

A sample 31 was obtained by the same method as in Example 30 except that Oregon pine wood flour was used instead of the eucalyptus chips for making paper.

Reference Example 2

A sample E was obtained by the same method as in Example 31 except that no meicelase (enzyme) was used.

Evaluation 14, Glucose Concentration

The glucose concentration of each of the samples 30, 31, D and E was measured after 33 hours. Specifically, 200 µL was taken out of each of the samples 30, 31, D and E (which were slurry or creamy), the supernatants after centrifugation were colored by Glucose Test Wako (manufactured by Wako Pure Chemical Industries, Ltd.), and the absorbances were measured using a spectrophotometer. Glucose concentrations were calculated, based on a previously prepared calibration curve, from the obtained absorbances.

The glucose concentrations obtained from the samples 30, 31, D and E are listed in Table 13.

TABLE 13

| Enzyme reaction time (hr) | Glucose concentration (mg/L) | | | |
|---|---|---|---|---|
| | Example 30 (Sample 30) | Reference Example 1 (Sample D) | Example 31 (Sample 31) | Reference Example 2 (Sample E) |
| 33 | 16800.8 | 36.9 | 26362.5 | 30.4 |

It was clear from the results of Table 13 that little glucose was generated in the system in which no enzyme was added in Reference Examples 1 and 2 whereas the glucose concentrations were significantly high and the enzymatic hydrolysis proceeded concurrently with the fibrillation in the system in which the enzyme was added in Examples 30 and 31.

Example 32

Using a eucalyptus which is a broad-leaved tree, as cellulosic material, the rough pulverization was performed to make 0.2 mm-pass eucalyptus wood flour by a cutter mill. Furthermore, the preliminary dry pulverization of the eucalyptus wood flour was carried out for 20 minutes to make the powdered fine cellulosic material.

Subsequently, 200 ml of water (fibrillation material) was added as a medium (eucalyptus wood flour in ten times the amount of water), and a lid was put on the planetary ball mill pot made of zirconia. In ball mill treatment, a cycle of treatment at an autorotation speed of 120 rpm for 20 minutes and stop for 10 minutes was repeated 100 times, and fibrillation treatment was performed for total treatment time of 33 hours to obtain a brown, creamy mixture. As the conditions of the fibrillation treatment, temperature and pulverization energy (gravitational acceleration) which can be applied to the ball in the container of the ball mill were set at 40° C. and 1.8 G at 120 rpm, respectively.

The water in the mixture was substituted with t-butylalcohol, and a dried sample 32 (fine fibrous cellulosic material; width of 0.05 μm and length of 5 μm) was obtained by drying under reduced pressure.

Example 33

A sample 33 (fine fibrous cellulosic material; average width of 0.03 μm and average length of 5 μm) was obtained by the same method as in Example 32 except that Oregon pine wood flour was used instead of the eucalyptus chips for making paper.

Evaluation 15, Hydrolysis

Glucose concentrations were calculated by the same method as in Evaluation 4 except that the samples 32 and 33 were used instead of the samples 1, 2 and A.

The glucose concentrations obtained from the samples 32 and 33 are listed in Table 14. The amounts of glucoses dissolved when suspending the samples in the acetate buffer prior to the charge of the enzyme are shown at enzyme reaction time of 0 hour.

TABLE 14

| Enzyme reaction time (hr) | Glucose concentration (mg/L) | |
|---|---|---|
| | Example 32 (Sample 32) | Example 33 (Sample 33) |
| 0 | 245.5 | 264.4 |
| 1 | 844.8 | 916.1 |
| 3 | 917.6 | 1395.7 |
| 6 | 924.6 | 1538.9 |
| 12 | 949.3 | 1579.0 |
| 18 | 971.5 | 1637.1 |
| 24 | 965.7 | 1664.8 |
| 36 | 979.0 | 1687.0 |
| 48 | 1008.9 | 1692.2 |

It was clear from the results of Table 14 that, when dry ball mill pulverization was carried out, followed by adding water as a fibrillation material to carry out the fibrillation treatment, enzymatic hydrolysis proceeded at extremely high speed and the reaction substantially completely proceeded after 6 hours of the enzymatic hydrolysis reaction.

Example 34

The rough pulverization of the Oregon pine chips for making paper as cellulosic materials was performed to make 3 mm-pass Oregon pine wood flour by a cutter mill. The resultant Oregon pine wood flour (500 g) was dispersed in 10 L of water, the dispersed substance was charged into Super Masscolloider (disk mill; disk material: silicon carbide; disk diameter: 10 inches; disk rotation number: 1,800 rpm; disk spacing: 200 μm; manufactured by Masuko Sangyo Co., Ltd.), and the fibrillation treatment was carried out for two minutes. Such fibrillation treatment was repeated five times (accumulated total treatment time: 10 minutes) to obtain a brown slurry mixture. As the condition of the fibrillation treatment, temperature was set at 45° C.

The water in the mixture was substituted with t-butylalcohol, and a dried sample 34 (fine fibrous cellulosic material; average width of 0.15 μm and average length of 15 μm) was obtained by drying under reduced pressure.

Example 35

A sample 35 (fine fibrous cellulosic material; average width of 0.1 μm and average length of 10 μm) was obtained by the same method as in Example 34 except that the fibrillation treatment was carried out ten times (accumulated total treatment time: 20 minutes).

Comparative Example 4

The rough pulverization using Oregon pine chips for making paper was performed to make 3 mm-pass Oregon pine wood flour by a cutter mill, and a sample F (fine fibrous cellulosic material; average width of 3,200 μm and average length of 3,200 μm) was obtained. No fibrillation treatment was carried out.

Evaluation 16, Microscopy

Scanning electron microscopy was performed by the same method as in Evaluation 2 except that the sample 35 was used instead of the sample 2.

Figure 4:
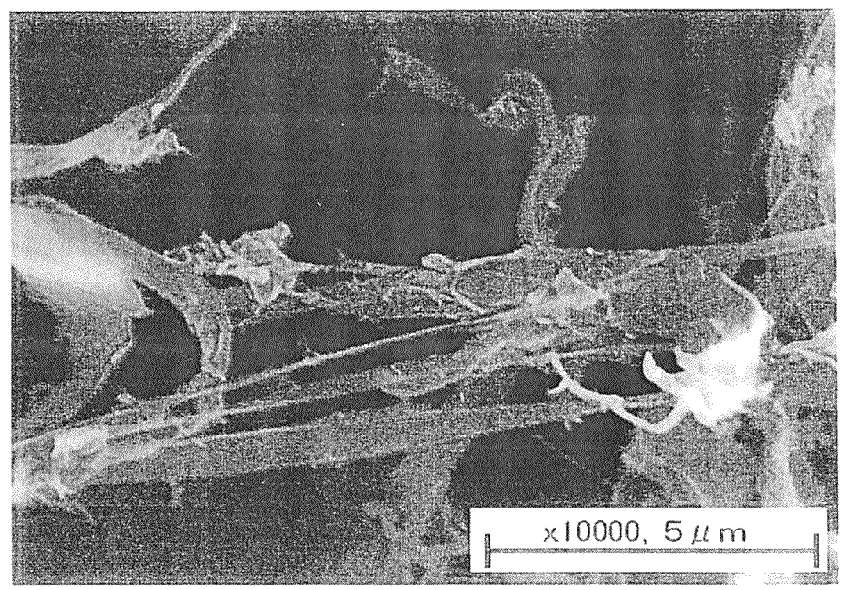
FIG. 4 is a scanning electron micrograph of a sample 35 obtained in Example 35.

The electron microscope photograph of the observation result of the obtained sample 35 is shown in FIG. 4.

As shown in FIG. 4, the fibrous cellulose of from around 100 nm to around 10 nm in the fine part was able to be observed. Further, the observation result of the sample 34 obtained in Example 34 was also similar (not shown).

Evaluation 17, Hydrolysis

Glucose concentrations were calculated by the same method as in Evaluation 4 except that the samples 34, 35 and F were used instead of the samples 1, 2 and A.

The glucose concentrations obtained from the samples 34, 35 and F are listed in Table 15. The amounts of glucoses dissolved when suspending the samples in the acetate buffer prior to the charge of the enzyme are shown at enzyme reaction time of 0 hour.

TABLE 15

| | Glucose concentration (mg/L) | | |
|---|---|---|---|
| Enzyme reaction time (hr) | Example 34 (Sample 34) | Example 35 (Sample 35) | Comparative Example 4 (Sample F) |
| 0 | 0.8 | 19.9 | 16.6 |
| 48 | 636.1 | 761.8 | 43.8 |

The results of Table 15 reveal that the enzymatic hydrolysis hardly proceeded in the sample F of Comparative Example 4 whereas the amount of generated glucose was increased in the sample 34 of Example 34 and the sample 35 of Example 35 and, particularly, the effect of improvement in enzymatic hydrolyzability was significantly observed in the sample 35 obtained by the increased number of times of the fibrillation treatment.

Example 36

The rough pulverization of the Oregon pine chips for making paper as cellulosic materials was performed to make 2 mm-pass Oregon pine wood flour by a cutter mill. The resultant Oregon pine wood flour (100 g) was mixed with ethylene glycol (200 g), and the mixture was charged into a twin-screw extruder (Labo-Prastomill; manufactured by Toyo Seiki Sei-saku-Sho, Ltd.), where a twin-screw multiple-thread flight type 2D20S was used as the screw. The fibrillation treatment was carried out by continuous extrusion at a speed of 30 rpm, and about 20 g of mixture was thus obtained for 10 minutes.

The water in the mixture was substituted with t-butylalcohol, and a dried sample 36 (fine fibrous cellulosic material; average width of 0.08 μm and average length of 10 μm) was obtained by drying under reduced pressure.

Example 37

A sample 37 (fine fibrous cellulosic material) was obtained by the same method as in Example 36 except that W-100 was used instead of the Oregon pine wood flour.

Reference Example 3

A sample G (fine fibrous cellulosic material) was obtained by the same method as in Example 36 except that no fibrillation treatment was carried out.

Reference Example 4

A sample H (fine fibrous cellulosic material) was obtained by the same method as in Example 37 except that no fibrillation treatment was carried out.

Evaluation 18, Microscopy

Scanning electron microscopy was performed by the same method as in Evaluation 2 except that the sample 36 was used instead of the sample 2.

Figure 5:
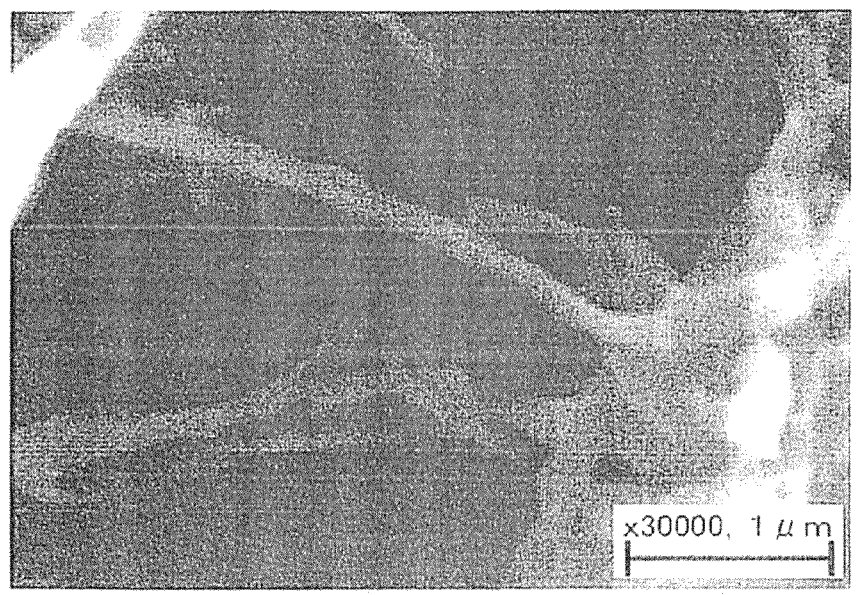
FIG. 5 is a scanning electron micrograph of a sample 36 obtained in Example 36.

The electron microscope photograph of the observation result of the obtained sample 36 is shown in FIG. 5.

As shown in FIG. 5, the fibrous cellulose of from around 100 nm to around 10 nm in the fine part was able to be observed.

Evaluation 19, Hydrolysis

Glucose concentrations were calculated by the same method as in Evaluation 4 except that the samples 36, 37, G and H were used instead of the samples 1, 2 and A.

The glucose concentrations obtained from the samples 36, 37, G and H are listed in Table 16.

TABLE 16

| | Glucose concentration (mg/L) | | | |
|---|---|---|---|---|
| Enzyme reaction time (hr) | Example 36 (Sample 36) | Reference Example 3 (Sample G) | Example 37 (Sample 37) | Reference Example 4 (Sample H) |
| 48 | 943.6 | 51.9 | 5217.3 | 2370.7 |

The comparison between Example 36 and Reference Example 3 reveals that the enzymatic hydrolysis hardly proceeded in the sample G of Reference Example 3 whereas the amount of generated glucose was increased and the effect of improvement in enzymatic hydrolyzability was observed in the sample 36 of Example 36.

Similarly, the comparison between Example 37 and Reference Example 4 reveals that the enzymatic hydrolysis proceeded to some extent in the sample H of Reference Example 4 whereas the amount of generated glucose was further increased and the effect of improvement in enzymatic hydrolyzability was observed in the sample 37 of Example 37.

The above results exhibit that, when the twin-screw extruder was used, the amount of generated glucose was significantly increased in the wood flour, the amount of generated glucose became twice or more even in the purified pulp, and the effect of improvement in enzymic hydrolyzability by fibrillation was observed.

Example 38

The rough pulverization of the Oregon pine chips for making paper as cellulosic materials was performed to make 2 mm-pass Oregon pine wood flour by a cutter mill. The resultant Oregon pine wood flour (100 g) was mixed with polyethylene glycol (5 g; molecular weight: 20,000), and the mixture was charged into a twin-screw extruder (Labo-Prastomill), where a twin-screw multiple-thread flight type 2D20S was used as the screw. The fibrillation treatment was carried out once at a temperature increased to 120° C. by continuous extrusion at a speed of 50 rpm, and about 30 g of mixture was thus obtained for 10 minutes.

The water in the mixture was substituted with t-butylalcohol, and a dried sample 38 (fine fibrous cellulosic material; average width of 0.3 μm and average length of 15 μm) was obtained by drying under reduced pressure.

Example 39

A sample 39 (fine fibrous cellulosic material; average width of 0.2 μm and average length of 15 μm) was obtained by the same method as in Example 38 except that the fibrillation treatment was carried out twice.

Evaluation 20, Hydrolysis

Glucose concentrations were calculated by the same method as in Evaluation 4 except that the samples 38 and 39 were used instead of the samples 1, 2 and A.

The glucose concentrations obtained from the samples 38 and 39 are listed in Table 17.

TABLE 17

| Enzyme reaction time (hr) | Glucose concentration (mg/L) | |
|---|---|---|
| | Example 38 (Sample 38) | Example 39 (Sample 39) |
| 48 | 291.8 | 506.4 |

The results of Table 17 reveal that the glucose concentration was increased with increasing the number of times of treatment with the twin-screw extruder, so that the effect of improvement in enzymatic hydrolyzability by fibrillation was observed.

Example 40

The rough pulverization of eucalyptus chips for making paper used as cellulosic materials was performed to make 0.2 mm-pass eucalyptus wood flour by a cutter mill. The resultant eucalyptus wood flour (1.5 g) was charged into a planetary ball mill pot made of zirconia (internal capacity: 45 ml), and seven zirconia balls having a diameter of 10 mm were filled thereinto.

Subsequently, 23 ml of aqueous solution of sodium hydroxide (2 wt %) was added as a medium, and a lid was put on the planetary ball mill pot made of zirconia. In ball mill treatment, a cycle of treatment at an autorotation speed of 200 rpm for 20 minutes and stop for 10 minutes was repeated 100 times, and fibrillation treatment was performed for total treatment time of 33 hours to obtain a brown, creamy mixture. As the conditions of the fibrillation treatment, temperature and pulverization energy which can be applied to the ball in the container of the ball mill were set at 40° C. and 1.8 G, respectively.

The water in the mixture was substituted with t-butylalcohol, and a dried sample 40 (fine fibrous cellulosic material; average width of 0.06 μm and average length of 10 μm) was obtained by drying under reduced pressure.

Example 41

A sample 41 (fine fibrous cellulosic material; average width of 0.07 μm and average length of 10 μm) was obtained by the same method as in Example 40 except that an aqueous solution of lithium hydroxide was used instead of the aqueous solution of sodium hydroxide.

Example 42

A sample 42 (fine fibrous cellulosic material; average width of 0.04 μm and average length of 15 μm) was obtained by the same method as in Example 40 except that Oregon pine wood flour was used instead of the eucalyptus wood flour.

Example 43

A sample 43 (fine fibrous cellulosic material; average width of 0.05 μm and average length of 15 μm) was obtained by the same method as in Example 42 except that an aqueous solution of lithium hydroxide was used instead of the aqueous solution of sodium hydroxide.

Evaluation 21, Hydrolysis

Glucose concentrations were calculated by the same method as in Evaluation 4 except that the samples 40 to 43 were used instead of the samples 1, 2 and A.

The glucose concentrations obtained from the samples 40 to 43 are listed in Table 18. The amounts of glucoses dissolved when suspending the samples in the acetate buffer prior to the charge of the enzyme are shown at enzyme reaction time of 0 hour.

TABLE 18

| Enzyme reaction time (hr) | Glucose concentration (mg/L) | | | |
|---|---|---|---|---|
| | Example 40 (Sample 40) | Example 41 (Sample 41) | Example 42 (Sample 42) | Example 43 (Sample 43) |
| 0 | 8.9 | 0.8 | 0.4 | 2.0 |
| 48 | 953.3 | 946.0 | 1130.6 | 1118.0 |

The results of Table 18 reveal that the amount of generated glucose was increased by adding an aqueous inorganic alkaline solution and the effect of improvement in enzymatic hydrolyzability by fibrillation was observed.

Example 44

The rough pulverization of eucalyptus chips for making paper used as cellulosic materials was performed to make 0.2 mm-pass eucalyptus wood flour by a cutter mill. The resultant eucalyptus wood flour (13.5 g) was charged into a planetary ball mill pot made of zirconia (internal capacity: 500 ml), and 25 zirconia balls having a diameter of 20 mm were filled thereinto.

Subsequently, 200 ml of water was added as a medium, and a lid was put on the planetary ball mill pot made of zirconia. In ball mill treatment, a cycle of treatment at an autorotation speed of 120 rpm for 20 minutes and stop for 10 minutes was repeated 100 times, and fibrillation treatment was performed for total treatment time of 33 hours to obtain a brown, creamy mixture. As the conditions of the fibrillation treatment, temperature and pulverization energy (gravitational acceleration) which can be applied to the ball in the container of the ball mill were set at 40° C. and 1.8 G at 120 rpm, respectively.

The water in the mixture was substituted with t-butylalcohol, and a dried sample 44 (fine fibrous cellulosic material; average width of 0.04 μm and average length of 7 μm) was obtained by drying under reduced pressure.

Example 45

The mixture obtained in Example 44 was used as a sample 45 (fine fibrous cellulosic material; average width of 0.04 μm and average length of 7 μm) without being processed, without being washed or dried.

Example 46

A sample 46 (fine fibrous cellulosic material; average width of 0.05 μm and average length of 15 μm) was obtained by the same method as in Example 44 except that Oregon pine wood flour was used instead of the eucalyptus wood flour.

Example 47

The mixture obtained in Example 46 was used as a sample 47 (fine fibrous cellulosic material; average width of 0.05 μm and average length of 15 μm) without being processed, without being washed or dried.

Evaluation 22, Hydrolysis

Glucose concentrations were calculated by the same method as in Evaluation 4 except that the samples 44 to 47 were used instead of the samples 1, 2 and A.

The glucose concentrations obtained from the samples 44 to 47 are listed in Table 19. The amounts of glucoses dissolved when suspending the samples in the acetate buffer prior to the charge of the enzyme are shown at enzyme reaction time of 0 hour.

TABLE 19

| Enzyme | Glucose concentration (mg/L) | | | |
|---|---|---|---|---|
| reaction time (hr) | Example 44 (Sample 44) | Example 45 (Sample 45) | Example 46 (Sample 46) | Example 47 (Sample 47) |
| 0 | 9.8 | 6.6 | 1.8 | 9.3 |
| 48 | 628.8 | 594.4 | 1021.9 | 1013.0 |

The results of Table 19 reveal that the washed and dried samples also exhibited enzymatic hydrolysis results similar to those of non-washed and non-dried samples and the effect of improvement in enzymatic hydrolyzability was observed.

This is likely to show that, when the washing and drying treatment of the samples was performed prior to the enzymatic hydrolysis, a slight amount of denatured substances and impurities contaminated in an aqueous medium in a fibrillation treatment step and contaminants in the fibrillation treatment were removed; however, their enzymic hydrolyzability was similar to that of the non-washed and non-dried samples, so that no factors of inhibiting the enzymatic hydrolysis due to the fibrillation treatment were able to be confirmed to occur.

Example 48

A test on improvement in enzymatic saccharification of woody biomass by fine fiberization using a small segment mixer (Labo-Prastomill KF15V; manfuactured by Toyo Seiki Seisaku-Sho, Ltd.) was conducted.

Figure 6A:
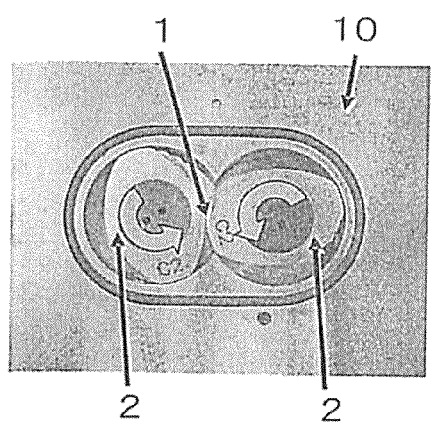
FIGS. 6 (*a*) and (*b*) are cross-sectional pictures for explaining the kneading portions of the small segment mixer used in Example 48.
Figure 6B:
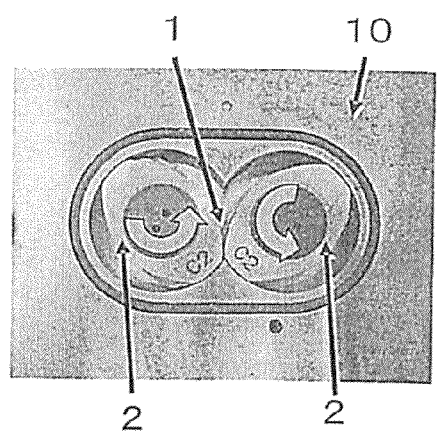

FIGS. 6 (a) and (b) are cross-sectional pictures for explaining the kneading portions of the small segment mixer.

As shown in FIG. 6, the small segment mixer 10 has the system of applying high shearing force and pressure to contents to open by the rotation of segment-type screws 2 in the same direction in the kneading portion 1. Thereby, the cellulosic material can be fibrillated to a nano-scale in water.

FIG. 7 (a) shows a front view of the segment-type screw and FIG. 7 (b) shows a side view of the segment-type screw.

As shown in FIG. 7, the segment-type screw 2 is capable of applying high shearing force by combining six segment blades overlapped by 22.5 degrees each. There are such combinations of various angles and shapes, which combinations are not limited to the combination shown in the figure.

First, Oregon pine wood flour subjected to rough pulverization to 2 mm-pass as a raw material was preliminarily pulverized for 5 minutes using a planetary ball mill. With 233 parts by mass of water, 100 parts by mass of the resultant preliminarily pulverized product was mixed, and the mixture was charged into the small segment mixer. As the conditions of the fibrillation treatment, temperature, pressure, screw speed and time were set at 40° C., about 0.5 MPa, 95 rpm and 20 minutes, respectively.

The mixture obtained by the fibrillation treatment was not washed or dried but was used as a sample 48 without being processed.

Comparative Example 5

Oregon pine wood flour subjected to rough pulverization to 2 mm-pass was used as a sample I (cellulosic material).

Evaluation 23, Hydrolysis

Glucose concentrations were calculated by the same method as in Evaluation 4 except that the samples 48 and I were used instead of the samples 1, 2 and A.

The glucose concentrations obtained from the samples 48 and I are listed in Table 20.

TABLE 20

| Enzyme | Glucose concentration (mg/L) | |
|---|---|---|
| reaction time (hr) | Example 48 (Sample 48) | Comparative Example 5 (Sample I) |
| 48 | 765.5 | 51.9 |

The results of Table 20 reveal that glucose is scarcely generated in non-treated 2 mm-Oregon pine wood flour whereas the glucose concentration become significantly high in the treatment product treated with the small segment mixer, indicating an effect of improvement in enzyme hydrolyzability by the fibrillation.

Evaluation 24, Microscopy

Scanning electron microscopy was performed by the same method as in Evaluation 2 except that the sample 48 was used instead of the sample 2.

The electron microscope photograph of the observation result of the obtained sample 48 is shown in FIG. 8.

As shown in FIG. 8, many fine fibers of 100 nm or less are clearly observed to be generated.

Example 49

The rough pulverization of eucalyptus chips for making paper used as a cellulosic material was performed to make 0.2 mm-pass eucalyptus wood flour by a cutter mill. The resultant eucalyptus wood flour (1.5 g) was immersed in 23 ml of water, left to stand for 24 hours, and then treated using an autoclave for sterilization at 121° C. for 60 minutes.

This treated product was left to stand to room temperature, the total amount thereof was then charged into a planetary ball mill pot made of zirconia (internal capacity: 45 ml; manfuactured by Fritsch Corporation (Germany)), seven zirconia balls having a diameter of 10 mm were filled thereinto, and a lid was put on the planetary ball mill pot. In ball mill treatment, a cycle of treatment at an autorotation speed of 400 rpm for 20 minutes and stop for 10 minutes was repeated six times, and fibrillation treatment was performed for total treatment time of 2 hours to obtain a brown, creamy mixture having a comparatively high flowability. As the conditions of the fibrillation treatment, temperature and pulverization energy which can be applied to the ball in the container of the ball mill were set at 40° C. and 7.8 G at 400 rpm, respectively.

The water in the mixture was substituted with t-butylalcohol, and a dried sample 49 (fine fibrous cellulosic material; average width of 0.04-0.09 μm and average length of 3-7 μm) was obtained by drying under reduced pressure.

Example 50

A sample 50 (fine fibrous cellulosic material; average width of 0.04-0.09 μm and average length of 3-7 μm) was obtained by the same method as in Example 49 except that treatment time with the autoclave for sterilization was set at 240 minutes.

Example 51

A sample 51 (fine fibrous cellulosic material; average width of 0.04-0.09 μm and average length of 3-7 μm) was obtained by the same method as in Example 49 except that treatment temperature with the autoclave for sterilization was set at 135° C.

Example 52

A sample 52 (fine fibrous cellulosic material; average width of 0.04-0.09 μm and average length of 3-7 μm) was obtained by the same method as in Example 51 except that treatment time with the autoclave for sterilization was set at 240 minutes.

Reference Example 5

A sample J was obtained by the same method as in Example 49 except that treatment with the autoclave for sterilization was carried out, followed by performing no fibrillation treatment.

Reference Example 6

A sample K was obtained by the same method as in Example 50 except that treatment with the autoclave for sterilization was carried out, followed by performing no fibrillation treatment.

Reference Example 7

A sample L was obtained by the same method as in Example 51 except that treatment with the autoclave for sterilization was carried out, followed by performing no fibrillation treatment.

Reference Example 8

A sample M was obtained by the same method as in Example 52 except that treatment with the autoclave for sterilization was carried out, followed by performing no fibrillation treatment.

Evaluation 24, Hydrolysis

Glucose concentrations were calculated by the same method as in Evaluation 4 except that the samples 49-52 and J-M were used instead of the samples 1, 2 and A.

The glucose concentrations obtained from the samples 49-52 and the glucose concentrations obtained from the samples J-M are listed in Table 21 and Table 22, respectively. Enzyme reaction time 0 hour indicates the amount of glucose dissolved when suspending a sample in an acetate buffer prior to charging an enzyme.

TABLE 21

| Enzyme reaction time (hr) | Glucose concentration (mg/L) | | | |
| --- | --- | --- | --- | --- |
| | Example 49 (Sample 49) | Example 50 (Sample 50) | Example 51 (Sample 51) | Example 52 (Sample 52) |
| 0 | 31.4 | 19.9 | 3.6 | 5.3 |
| 48 | 540.6 | 605.7 | 1020.7 | 1301.2 |

TABLE 22

| Enzyme reaction time (hr) | Glucose concentration (mg/L) | | | |
| --- | --- | --- | --- | --- |
| | Reference Example 5 (Sample J) | Reference Example 6 (Sample K) | Reference Example 7 (Sample L) | Reference Example 8 (Sample M) |
| 0 | 1.6 | 5.3 | 4.3 | 12.5 |
| 48 | 64.5 | 70.1 | 75.2 | 83.2 |

The results of Tables 21 and 22 reveal that the hydrothermal treatment with the autoclave for sterilization resulted in the partial hydrolysis of the tissue of the eucalyptus wood flour to embrittle the rigid ingredient network, the ball mill pulverization facilitated the proceeding of fine fiberization, and an enzymatic saccharification property was improved.

Example 53

The rough pulverization of straw as a cellulosic material was performed to make 3 mm-pass by a cutter mill. The resultant pulverized crude straw product (1.5 g) together with 23 ml of water was charged into a planetary ball mill pot made of zirconia (internal capacity: 45 ml; manufactured by Fritsch Corporation (Germany)), seven zirconia balls having a diameter of 10 mm were filled thereinto, and a lid was put on the planetary ball mill pot. In ball mill treatment, a cycle of treatment at an autorotation speed of 400 rpm for 20 minutes and stop for 10 minutes was repeated six times, and fibrillation treatment was performed for total treatment time of 2 hours to obtain a brown, creamy mixture having a comparatively high flowability. As the conditions of the fibrillation treatment, temperature and pulverization energy which can be applied to the ball in the container of the ball mill were set at 40° C. and 7.8 G at 400 rpm, respectively.

The water in the mixture was substituted with t-butylalcohol, and a dried sample 53 (fine fibrous cellulosic material; average width of 0.05 μm and average length of 6 μm) was obtained by drying under reduced pressure.

Example 54

A sample 54 (fine fibrous cellulosic material; average width of 0.04 μm and average length of 4 μm) was obtained by the same method as in Example 53 except that straw subjected to rough pulverization to 0.2 mm-pass by a cutter mill was used.

Evaluation 25, Hydrolysis

Glucose concentrations were calculated by the same method as in Evaluation 4 except that the samples 53 and 54 were used instead of the samples 1, 2 and A.

The glucose concentrations obtained from the samples 53 and 54 are listed in Table 23. Enzyme reaction time 0 hour indicates the amount of glucose dissolved when suspending a sample in an acetate buffer prior to charging an enzyme.

TABLE 23

| Enzyme reaction time (hr) | Glucose concentration (mg/L) | |
| --- | --- | --- |
| | Example 53 (Sample 53) | Example 54 (Sample 54) |
| 0 | 8.1 | 26.0 |
| 48 | 647.9 | 685.6 |

The results of Table 23 reveal that, even when using straw as a raw material, fine fiberization was allowed by fibrillation treatment to improve an enzymatic saccharification property.

Example 55

The rough pulverization of eucalyptus chips for making paper used as a cellulosic material was performed to make 3 mm-pass eucalyptus wood flour by a cutter mill. The resultant eucalyptus wood flour (about 1 kg) was immersed in 10 L of water, left to stand for 24 hours, and then treated using an autoclave for sterilization at 135° C. for 240 minutes.

This treated product was left to stand to room temperature, water was added so that a solid content concentration of the eucalyptus wood flour was 5 mass %, 20 L of resultant dispersion was charged into Super Masscolloider (disk mill; disk material: silicon carbide; disk diameter: 10 inches; disk rotation number: 1,800 rpm; disk spacing: 200 μm; manufactured by Masuko Sangyo Co., Ltd.), and the fibrillation treatment was carried out for 4 minutes to obtain a brown slurry mixture. As the condition of the fibrillation treatment, temperature was set at 45° C.

The water in the mixture was substituted with t-butylalcohol, and a dried sample 55 (fine fibrous cellulosic material; average width of 0.1 μm and average length of 10 μm) was obtained by drying under reduced pressure.

Example 56

A sample 56 (fine fibrous cellulosic material; average width of 0.1 μm and average length of 10 μm) was obtained by the same method as in Example 55 except that fibrillation treatment was repeated ten times (accumulated total treatment time: 40 minutes).

Example 57

A sample 57 (fine fibrous cellulosic material; average width of 0.15 μm and average length of 15 μm) was obtained by the same method as in Example 55 except that the rough pulverization of eucalyptus chips for making paper was performed to make 0.2 mm-pass eucalyptus wood flour by a cutter mill and no treatment using the autoclave for sterilization was carried out.

Example 58

A sample 58 (fine fibrous cellulosic material; average width of 0.15 μm and average length of 15 μm) was obtained by the same method as in Example 57 except that fibrillation treatment was repeated ten times (accumulated total treatment time: 40 minutes).

Evaluation 26, Hydrolysis

Glucose concentrations were calculated by the same method as in Evaluation 4 except that the samples 55-58 were used instead of the samples 1, 2 and A.

The glucose concentrations obtained from the samples 55-58 are listed in Table 24. Enzyme reaction time 0 hour indicates the amount of glucose dissolved when suspending a sample in an acetate buffer prior to charging an enzyme.

TABLE 24

| Enzyme reaction time (hr) | Glucose concentration (mg/L) | | | |
| --- | --- | --- | --- | --- |
| | Example 55 (Sample 55) | Example 56 (Sample 56) | Example 57 (Sample 57) | Example 58 (Sample 58) |
| 0 | 6.1 | 14.7 | 4.1 | 61.7 |
| 48 | 315.8 | 430.8 | 76.3 | 271.8 |

The results of Table 24 reveal that the hydrothermal treatment with the autoclave for sterilization resulted in the partial hydrolysis of the tissue of the eucalyptus wood flour to embrittle the rigid ingredient network, the disk mill pulverization facilitated the proceeding of fine fiberization in a short time (small number of treatments), and an enzymatic saccharification property was improved.

Example 59

The rough pulverization of straw as a cellulosic material was performed to make 3 mm-pass by a cutter mill. The resultant pulverized crude straw product (1.5 g) together with 23 ml of water was charged into a planetary ball mill pot made of zirconia (internal capacity: 45 ml; manufactured by Fritsch Corporation (Germany)), and 25 zirconia balls having a diameter of 20 mm were filled thereinto.

Subsequently, 300 ml of water was added as a medium, and a lid was put on the planetary ball mill pot. In ball mill treatment, a cycle of treatment at an autorotation speed of 120 rpm for 20 minutes and stop for 10 minutes was repeated 100 times, and fibrillation treatment was performed for total treatment time of 33 hours to obtain a brown, creamy mixture. As the conditions of the fibrillation treatment, temperature and pulverization energy (gravitational acceleration) which can be applied to the ball in the container of the ball mill were set at 40° C. and 1.8 G at 120 rpm, respectively.

To concentrate the solid content in the mixture, centrifugation was carried out on the conditions of 7,000 rpm and 15 minutes, and precipitates were collected to obtain a clayey product. The water content of the clayey product was 76% when measured by a halogen aquameter.

Subsequently, 12.8 g of clayey product was charged into a high-pressure autoclave having an internal capacity of 57 ml, 3.6 g of ethanol and 0.14 g of acetic acid were added, and the autoclave was shut tightly. A ratio between water and ethanol contained in the clayey product was 7.5/2.5. A ratio between a solid content and a liquid content was 1/5.

Then, heat treatment was carried out by a heater at 180° C. for 15 minutes. The resultant treated product was then filtered, and a solid content on the filter paper, equivalent to a dry weight of 50 mg, was measured, without performing a drying operation, to obtain a sample 59.

Example 60

A sample 60 was obtained by the same method as in Example 59 except that the heat treatment with the heater was performed for 60 minutes.

Evaluation 27, Hydrolysis

Glucose concentrations were calculated by the same method as in Evaluation 4 except that the samples 59 and 60 were used instead of the samples 1, 2 and A.

The glucose concentrations obtained from the samples 59 and 60 are listed in Table 25. Enzyme reaction time 0 hour indicates the amount of glucose dissolved when suspending a sample in an acetate buffer prior to charging an enzyme.

TABLE 25

| Enzyme reaction time (hr) | Glucose concentration (mg/L) | |
| --- | --- | --- |
| | Example 59 (Sample 59) | Example 60 (Sample 60) |
| 0 | 12.3 | 25.7 |
| 48 | 1868.9 | 2045.8 |

The results of Table 25 reveal that an enzymatic saccharification property was significantly improved by heat treatment with water, ethanol and acetic acid after the fibrillation treatment.

This means that heat treatment in a predetermined liquid after the fibrillation treatment is extremely effective.

Example 61

With 300 parts by mass of water, 100 parts of switchgrass (a type of grass) having a size of 2 mm was mixed, the mixture was prepared, and the mixture was charged into a twin-screw extruder (Labo-Prastomill; manufactured by Toyo Seiki Seisaku-Sho, Ltd.), where a twin-screw multiple-thread flight type 2D20S was used as the screw. The twin-screw extruder was continuously operated at the rate of 30 rpm at room temperature.

The mixture was then taken out of the twin-screw extruder and 50 mg on a solid content basis was put in 15 ml of acetate buffer solution, and a solution in which 2 mg of cellulase (trade name: meicelase; manufactured by Meiji Seika Kaisha, Ltd.) was dissolved in 2 ml of acetate buffer solution was further added, and enzymatic hydrolysis (saccharification) was performed at 45° C. for 48 hours to obtain a sample 61.

Comparative Example 6

Switchgrass subjected to rough pulverization to 0.2 mm-pass was used as a sample O.

Evaluation 28, Analysis of Obtained Saccharide

In the sample 61, saccharides were identified using high performance liquid chromatograph (LC-2000 Puls HPLC System made by JASCO Corporation; sample injection rate: 20 µl; detection: refractive index detector; column: Aminex HPX-87P (Bio-Rad); column temperature: 80° C.; flow rate: 1.0 ml/min), and the concentrations of the respective saccharides were quantified from calibration curves made using preparations.

The obtained results are listed in Table 26.

TABLE 26

| | Alpha-cellulose | Hemicellulose | Lignin | Ash |
| --- | --- | --- | --- | --- |
| Amount (wt. %) | 33.2 | 25.0 | 22.0 | 2.9 |

The results of Table 26 reveal that the switchgrass contained alpha-cellulose of 33.2%, which was a lower value than that of Oregon pine or eucalyptus.

Evaluation 29, Hydrolysis

Glucose concentrations were calculated by the same method as in Evaluation 4 except that the samples 61 and O were used instead of the samples 1, 2 and A.

The glucose concentrations obtained from the samples 61 and O are listed in Table 27.

TABLE 27

| Enzyme reaction time (hr) | Glucose concentration (mg/L) | |
| --- | --- | --- |
| | Example 61 (Sample 61) | Comparative Example 6 (Sample O) |
| 48 | 390.2 | 20.9 |

The results of Table 27 reveal that the enzymatic saccharification rate of the sample 61 in Example 61 using the twin-screw extruder was about 20 times higher than that of the sample O in Comparative Example 6.

Evaluation 30, Hydrolysis

An enzymatic hydrolysis reaction was carried out according to the method of Evaluation 4 using the samples 61 and O instead of the samples 1, 2 and A, and xylose concentrations were calculated by the method of Evaluation 28.

The xylose concentrations obtained from the samples 61 and O are listed in Table 28.

TABLE 28

| Enzyme reaction time (hr) | Xylose concentration (mg/L) | |
| --- | --- | --- |
| | Example 61 (Sample 61) | Comparative Example 6 (Sample O) |
| 48 | 79.5 | Almost zero |

The results of Table 27 reveal that the sample 61 of Example 61 using the twin-screw extruder generated a large amount (79.5 mg/L) of xylose although meicelase (Meiji Seika Kaisha, Ltd.) containing a small amount of hemicellulase was used.

Based on the above results, the fine fibrous cellulosic material of the present invention was confirmed to allow the production of a saccharide in a high yield by hydrolysis.

INDUSTRIAL APPLICABILITY

The fine fibrous cellulose of the present invention can be used not only in the production of a saccharide or ethanol from the saccharide but also as a high-strength material by being conjugated as a filler to a resin or the like because of having an extremely high strength in terms of a molecular structure.

The fine fibrous cellulose can be also converted into a high-strength material without being processed, without any operation such as the use of an adhesive or the chemical denaturalization of the fine fibrous cellulose, because of having strong self-cohesive power.

In addition, since the fine fibrous cellulose is a natural product, has neither taste nor odor, is atoxic, has fine fibers and therefore offers no foreign body feeling on the tongue, the fine fibrous cellulose can be added to a food product to be imparted with water retentivity, oil retentivity, texture, morphological stability or dietetic properties.

What is claimed is:

1. A process for producing a fine fibrous cellulosic material suitable for a hydrolytic glycation reaction, comprising the steps of:
   preliminarily pulverizing a cellulosic material containing cellulose, hemicellulose and lignin to make a fibrous or powdered fine cellulosic material;
   mixing the fine cellulosic material with a fibrillation material constituted of water and an inorganic alkali to form a mixture, the inorganic alkali constituting from 0.1-99.9% of the total weight of the fibrillation material and being at least one member selected from the group consisting of lithium hydroxide, sodium hydroxide and potassium hydroxide; and carrying out mechanical pulverization of the mixture to produce a fine, fibrous cellulosic material having a width of no more than 1 μm and a length of no more than 5,000 μm.

2. The process for producing a fine fibrous cellulosic material according to claim 1, wherein the mechanical pulverization is performed by a ball mill, a rod mill, a bead mill, a disk mill or a mixer.

3. The process for producing a fine fibrous cellulosic material according to claim 1, wherein the mechanical pulverization is performed by a batch-type or continuous-type extruder.

4. The process for producing a fine fibrous cellulosic material according to claim 3, characterized in that the mechanical pulverization is performed under a temperature condition of 20-350° C. and/or a pressure condition of 0.1-20 MPa.

5. The process for producing a fine fibrous cellulosic material according to claim 1, wherein a mixing rate of the fibrillation material is 0.01-200 parts by mass with respect to 1 part by mass of cellulosic material.

* * * * *